(12) United States Patent
Reilly et al.

(10) Patent No.: US 8,686,016 B2
(45) Date of Patent: Apr. 1, 2014

(54) SCHWEINFURTHINS AND USES THEREOF

(75) Inventors: Karlyne Reilly, Potomac, MD (US); Thomas Turbyville, Frederick, MD (US); John A. Beutler, Union Bridge, MD (US); David Wiemer, Iowa City, IA (US)

(73) Assignees: The United States of America, as represented by the Secretary, Department of Health and Human Services, Washington, DC (US); University of Iowa Research Foundation, Iowa City, IA (US)

( * ) Notice: Subject to any disclaimer, the term of this patent is extended or adjusted under 35 U.S.C. 154(b) by 131 days.

(21) Appl. No.: 13/266,841

(22) PCT Filed: Apr. 30, 2010

(86) PCT No.: PCT/US2010/033153
§ 371 (c)(1),
(2), (4) Date: Dec. 20, 2011

(87) PCT Pub. No.: WO2010/127235
PCT Pub. Date: Nov. 4, 2010

(65) Prior Publication Data
US 2012/0095089 A1 Apr. 19, 2012

Related U.S. Application Data

(60) Provisional application No. 61/174,338, filed on Apr. 30, 2009.

(51) Int. Cl.
*A61K 31/352* (2006.01)
*C07D 311/82* (2006.01)

(52) U.S. Cl.
USPC .......................................... 514/388; 549/388

(58) Field of Classification Search
None
See application file for complete search history.

(56) References Cited

U.S. PATENT DOCUMENTS

| 7,358,377 B2 | 4/2008 | Wiemer et al. |
| 7,902,228 B2 | 3/2011 | Wiemer et al. |
| 2008/0227852 A1 | 9/2008 | Wiemer et al. |

FOREIGN PATENT DOCUMENTS

| WO | WO 2005/092878 A2 | 10/2005 |
| WO | WO 2009/158516 A1 | 12/2009 |

OTHER PUBLICATIONS

Callahan et al., "MEDI 173 Effects of C-ring substitution on the pharmacophore of the schweinfurthins," CAS abstract, 2007, accession No. 2007:295606 (containing chemical structures), presented at 233rd American Chemical Society National Meeting, Mar. 25-29, 2007.
Neighbors et al., "MEDI 172 Probing the mechanism of 3-deoxyschweinfurthin B anticancer activity via fluorescence microscopy," CAS abstract, presented at 233rd American Chemical Society National Meeting, Mar. 25-29, 2007.
140th National Cancer Advisory Board, Summary of Meeting of Nov. 30-Dec. 1, 2006, which was published online no later than May 6, 2007 (40 pages).
Beutler et al., *Journal of Natural Products*, 1998, 61:1509-1512, published online Oct. 24, 1998.
Beutler slide presentation presented at Northeastern University, May 21, 2009 (36 pages).
Callahan, CAS, abstract, 2007, accession No. 2007:295606.
*Children's Tumor Foundation 2007 Annual Financial Report.*
*Children's Tumor Foundation 2008 Annual Financial Report.*
*Children's Tumor Foundation 2008 Annual Report.*
*Children's Tumor Foundation 2008 Neurofibromatosis Conference* (Jun. 6-10, 2008) *Summary.*
*Children's Tumor Foundation Neurofibromatosis News*, 28(3), published Summer 2007.
*Children's Tumor Foundation Neurofibromatosis News*, 29(3), published Summer 2008.
Cui et al., *Conf Proc IEEE Eng Med Biol Soc.*, 2009, 2009:5768-71.
Klausmeyer et al., *J. Nat. Prod.*, 2010, 73:479-81 (NIH public access author manuscript).
Kodet et al., 236th American Cancer Society Annual Meeting, Abstract of Meeting, Aug. 18-21, 2008.
Kuder, Dissertation, University of Iowa, Dec. 2009.
Kuder et al., *Bioorg Med Chem.*, 2009, 17:4718-23., published online May 6, 2009.
Mente et al., *Bioorganic & Medicinal Chemistry*, 2007, 17:911-915, published online Dec. 12, 2006.
Mente et al., *J. Org. Chem.*, 2008, 73:7963-70, published online Sep. 17, 2008.
NCI grant summary Z01 BC 010541 (Z01), available online Oct. 2008.

(Continued)

*Primary Examiner* — Bernard Dentz
(74) *Attorney, Agent, or Firm* — Leydig, Voit & Mayer, Ltd.

(57) ABSTRACT

Disclosed is a method for preventing or treating an undesirable condition in a subject carrying cells homozygous null for the neurofibromatosis type 1 gene or subjects that are haploinsufficient for the neurofibromatosis type 1 gene, the method comprising administering to a subject in need thereof an effective amount of a schweinfurthin or schweinfurthin analog or derivative, or a pharmaceutically acceptable salt, prodrug, hydrate, or solvate thereof. Also disclosed is a new schweinfurthin compound of the formula.

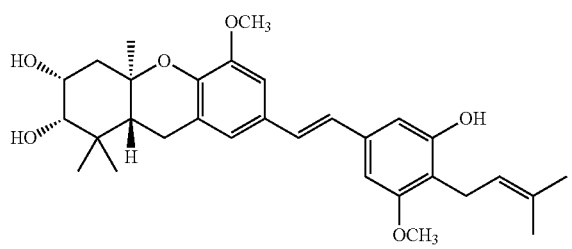

22 Claims, 17 Drawing Sheets

(56) References Cited

OTHER PUBLICATIONS

Neighbors et al., *Bioorganic & Medicinal Chemistry*, 2006, 14:1771-1784, published online Nov. 14, 2005.
Neighbors et al., *J. Org. Chem.*, 2005, 70:925-931, published online Jan. 11, 2005.
Neighbors et al., *Tetrahedron Lett.*, 2008, 49:516-519, published online Nov. 21, 2007.
Neighbors et al., U.S. Army Medical Research and Materiel Command, Date of report: May 2005 (62 pages). [While the exact publication date is unknown, please treat as prior art.].
PCT/US2010/033153 International Preliminary Report on Patentability, Nov. 10, 2011.
PCT/US2010/033153 International Search Report dated Jul. 30, 2010.
Reilly, abstract, Jun. 14, 2009, Children Tumor Foundation Meeting in Portland, Oregon.
Reilly et al., *Cancer Res.*, 2006, 66:62-8.
Reilly et al., *Nat. Genet.*, 2000, 26:109-13.
Topczewski et al., *J. Org. Chem.*, 2009, 74:6965-72, published online Aug. 21, 2009.
Treadwell et al., *J. Org. Chem.*, 1999, 64:8718-8723, published online Nov. 12, 1999.
Treadwell et al., *Organic Letters*, 2002, 4:3639-3642, published online Sep. 19, 2002.
Turbyville et al., 2008 NF Conference, abstract, Jun. 6-10, 2008.
Turbyville et al., *Molecular Cancer Therapeutics*, 2010, 9:1234-1243, published online May 4, 2010.
Ulrich et al., *Bioorganic & Medicinal Chemistry*, 2010, 18:1676-1683, published online Jan. 4, 2010.
Ulrich et el., MIKI 2008 poster, 2008 Medicinal Chemistry Meeting-in-Miniature "MIKI" Meeting, Apr. 25-27, 2008.
Ulrich et al., The $42^{nd}$ Annual American Cancer Society Midwest Regional Meeting, abstract, Nov. 8, 2007.
Ulrich, The $10^{th}$ Annual James F. Jakobsen Conference, abstract (p. 36), Mar. 28-29, 2008.
Ulrich et al., The $10^{th}$ Annual James F. Jakobsen Conference, poster, Mar. 28-29, 2008, also presented at ACS Regional Meeting, Nov. 7-10, 2007.
Yoder et al., *J. Nat. Prod.*, 2007, 70:342-346, published online Feb. 28, 2007.

SEQUENCE LISTING

<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gacgagcagc ttccaataaa                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
acttcggaat tctgcctctg                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
aagccctcac aacaaccaac                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tggttgcggg aaatattgat                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
atgactggct tcctttgtgc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ttgatggaag ccaaatcaca                                              20

<210> SEQ ID NO 7
<211> LENGTH: 20
<212> TYPE: DNA

```
<213> ORGANISM: Artificial Sequence
<220> FEATURE:
<223> OTHER INFORMATION: Synthetic

<400> SEQUENCE: 7
cacatcctct gattggcaac                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tcttgcatac ctgggtcctc                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
agcagagcga acaaaagtcc                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tgatgccaaa cgacaaagag                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
taccgggaca ggtcattctc                                                  20

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
aactttgcat tggttggaca c                                                21

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
caacagcacc cacatttacg                                                  20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
aggaatcgac aaggagaacg                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccataaagcc acagacaagg                                                    20

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
gcagatccaa tttctttgtg g                                                  21

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
aaaccatcca ccaagtcaaa                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
cttaggccac caatccaatg                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ctgcatcctg ctgcactatc                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic

```
<400> SEQUENCE: 20
catgggtggg ctataggttg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
tgcgcacttt catcttcaac                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
aaacagtggc acacacttcg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tggaagtccc agcttggtag                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cacactcctg gtgcatgaag                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cacctgttgc actggttttg                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
atgcctccat gatctccaac                                              20

<210> SEQ ID NO 27
<211> LENGTH: 20
<212> TYPE: DNA
```

<213> ORGANISM: Artificial Sequence
<220> FEATURE:
<223> OTHER INFORMATION: Synthetic

<400> SEQUENCE: 27
gctaagtagg ccacgctctg                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tttgggaaac acaacactgg                                                    20

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
gaaagcaagc aagcttcaca c                                                  21

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
tggtcgcact tattttcctg                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
agggaacctg ggagtagagg                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
aacactgggt tgtgggagag                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
agacggccca gaggagttag                                                    20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
cttcccttcc tttcctccag    20

<210> SEQ ID NO 35
<211> LENGTH: 38
<212> TYPE: DNA
<213> ORGANISM: Artificial Sequence
<220> FEATURE:
<223> OTHER INFORMATION: Synthetic

<400> SEQUENCE: 35
tgtaaaacga cggccagtga cgagcagctt ccaataaa    38

<210> SEQ ID NO 36
<211> LENGTH: 38
<212> TYPE: DNA
<213> ORGANISM: Artificial Sequence
<220> FEATURE:
<223> OTHER INFORMATION: Synthetic

<400> SEQUENCE: 36
tgtaaaacga cggccagtac ttcggaattc tgcctctg    38

<210> SEQ ID NO 37
<211> LENGTH: 38
<212> TYPE: DNA
<213> ORGANISM: Artificial Sequence
<220> FEATURE:
<223> OTHER INFORMATION: Synthetic

<400> SEQUENCE: 37
tgtaaaacga cggccagtaa gccctcacaa caaccaac    38

<210> SEQ ID NO 38
<211> LENGTH: 38
<212> TYPE: DNA
<213> ORGANISM: Artificial Sequence
<220> FEATURE:
<223> OTHER INFORMATION: Synthetic

<400> SEQUENCE: 38
tgtaaaacga cggccagttg gttgcgggaa atattgat    38

<210> SEQ ID NO 39
<211> LENGTH: 38
<212> TYPE: DNA
<213> ORGANISM: Artificial Sequence
<220> FEATURE:
<223> OTHER INFORMATION: Synthetic

<400> SEQUENCE: 39
tgtaaaacga cggccagtat gactggcttc ctttgtgc    38

<210> SEQ ID NO 40
<211> LENGTH: 38
<212> TYPE: DNA
<213> ORGANISM: Artificial Sequence
<220> FEATURE:
<223> OTHER INFORMATION: Synthetic

<400> SEQUENCE: 40
tgtaaaacga cggccagttt gatggaagcc aaatcaca                              38

<210> SEQ ID NO 41
<211> LENGTH: 38
<212> TYPE: DNA
<213> ORGANISM: Artificial Sequence
<220> FEATURE:
<223> OTHER INFORMATION: Synthetic

<400> SEQUENCE: 41
tgtaaaacga cggccagtca catcctctga ttggcaac                              38

<210> SEQ ID NO 42
<211> LENGTH: 38
<212> TYPE: DNA
<213> ORGANISM: Artificial Sequence
<220> FEATURE:
<223> OTHER INFORMATION: Synthetic

<400> SEQUENCE: 42
tgtaaaacga cggccagttc ttgcatacct gggtcctc                              38

<210> SEQ ID NO 43
<211> LENGTH: 38
<212> TYPE: DNA
<213> ORGANISM: Artificial Sequence
<220> FEATURE:
<223> OTHER INFORMATION: Synthetic

<400> SEQUENCE: 43
tgtaaaacga cggccagtag cagagcgaac aaaagtcc                              38

<210> SEQ ID NO 44
<211> LENGTH: 38
<212> TYPE: DNA
<213> ORGANISM: Artificial Sequence
<220> FEATURE:
<223> OTHER INFORMATION: Synthetic

<400> SEQUENCE: 44
tgtaaaacga cggccagttg atgccaaacg acaaagag                              38

<210> SEQ ID NO 45
<211> LENGTH: 38
<212> TYPE: DNA
<213> ORGANISM: Artificial Sequence
<220> FEATURE:
<223> OTHER INFORMATION: Synthetic

<400> SEQUENCE: 45
tgtaaaacga cggccagtta ccgggacagg tcattctc                              38

<210> SEQ ID NO 46
<211> LENGTH: 39
<212> TYPE: DNA
<213> ORGANISM: Artificial Sequence
<220> FEATURE:
<223> OTHER INFORMATION: Synthetic

<400> SEQUENCE: 46
tgtaaaacga cggccagtaa ctttgcattg gttggacac                             39

<210> SEQ ID NO 47
<211> LENGTH: 38
<212> TYPE: DNA

```
<213> ORGANISM: Artificial Sequence
<220> FEATURE:
<223> OTHER INFORMATION: Synthetic

<400> SEQUENCE: 47
tgtaaaacga cggccagtca acagcaccca catttacg                              38

<210> SEQ ID NO 48
<211> LENGTH: 38
<212> TYPE: DNA
<213> ORGANISM: Artificial Sequence
<220> FEATURE:
<223> OTHER INFORMATION: Synthetic

<400> SEQUENCE: 48
tgtaaaacga cggccagtag gaatcgacaa ggagaacg                              38

<210> SEQ ID NO 49
<211> LENGTH: 38
<212> TYPE: DNA
<213> ORGANISM: Artificial Sequence
<220> FEATURE:
<223> OTHER INFORMATION: Synthetic

<400> SEQUENCE: 49
tgtaaaacga cggccagtcc ataaagccac agacaagg                              38

<210> SEQ ID NO 50
<211> LENGTH: 39
<212> TYPE: DNA
<213> ORGANISM: Artificial Sequence
<220> FEATURE:
<223> OTHER INFORMATION: Synthetic

<400> SEQUENCE: 50
tgtaaaacga cggccagtgc agatccaatt tctttgtgg                             39

<210> SEQ ID NO 51
<211> LENGTH: 37
<212> TYPE: DNA
<213> ORGANISM: Artificial Sequence
<220> FEATURE:
<223> OTHER INFORMATION: Synthetic

<400> SEQUENCE: 51
caggaaacag ctatgacaaa ccatccacca agtcaaa                               37

<210> SEQ ID NO 52
<211> LENGTH: 37
<212> TYPE: DNA
<213> ORGANISM: Artificial Sequence
<220> FEATURE:
<223> OTHER INFORMATION: Synthetic

<400> SEQUENCE: 52
caggaaacag ctatgacctt aggccaccaa tccaatg                               37

<210> SEQ ID NO 53
<211> LENGTH: 37
<212> TYPE: DNA
<213> ORGANISM: Artificial Sequence
<220> FEATURE:
<223> OTHER INFORMATION: Synthetic

<400> SEQUENCE: 53
caggaaacag ctatgacctg catcctgctg cactatc                               37
```

<210> SEQ ID NO 54
<211> LENGTH: 37
<212> TYPE: DNA
<213> ORGANISM: Artificial Sequence
<220> FEATURE:
<223> OTHER INFORMATION: Synthetic

<400> SEQUENCE: 54
caggaaacag ctatgaccat gggtgggcta taggttg					37

<210> SEQ ID NO 55
<211> LENGTH: 37
<212> TYPE: DNA
<213> ORGANISM: Artificial Sequence
<220> FEATURE:
<223> OTHER INFORMATION: Synthetic

<400> SEQUENCE: 55
caggaaacag ctatgactgc gcactttcat cttcaac					37

<210> SEQ ID NO 56
<211> LENGTH: 37
<212> TYPE: DNA
<213> ORGANISM: Artificial Sequence
<220> FEATURE:
<223> OTHER INFORMATION: Synthetic

<400> SEQUENCE: 56
caggaaacag ctatgacaaa cagtggcaca cacttcg					37

<210> SEQ ID NO 57
<211> LENGTH: 37
<212> TYPE: DNA
<213> ORGANISM: Artificial Sequence
<220> FEATURE:
<223> OTHER INFORMATION: Synthetic

<400> SEQUENCE: 57
caggaaacag ctatgactgg aagtcccagc ttggtag					37

<210> SEQ ID NO 58
<211> LENGTH: 37
<212> TYPE: DNA
<213> ORGANISM: Artificial Sequence
<220> FEATURE:
<223> OTHER INFORMATION: Synthetic

<400> SEQUENCE: 58
caggaaacag ctatgaccac actcctggtg catgaag					37

<210> SEQ ID NO 59
<211> LENGTH: 37
<212> TYPE: DNA
<213> ORGANISM: Artificial Sequence
<220> FEATURE:
<223> OTHER INFORMATION: Synthetic

<400> SEQUENCE: 59
caggaaacag ctatgaccac ctgttgcact ggttttg					37

<210> SEQ ID NO 60
<211> LENGTH: 37
<212> TYPE: DNA
<213> ORGANISM: Artificial Sequence
<220> FEATURE:
<223> OTHER INFORMATION: Synthetic

```
<400> SEQUENCE: 60
caggaaacag ctatgacatg cctccatgat ctccaac                              37

<210> SEQ ID NO 61
<211> LENGTH: 37
<212> TYPE: DNA
<213> ORGANISM: Artificial Sequence
<220> FEATURE:
<223> OTHER INFORMATION: Synthetic

<400> SEQUENCE: 61
caggaaacag ctatgacgct aagtaggcca cgctctg                              37

<210> SEQ ID NO 62
<211> LENGTH: 37
<212> TYPE: DNA
<213> ORGANISM: Artificial Sequence
<220> FEATURE:
<223> OTHER INFORMATION: Synthetic

<400> SEQUENCE: 62
caggaaacag ctatgacttt gggaaacaca acactgg                              37

<210> SEQ ID NO 63
<211> LENGTH: 38
<212> TYPE: DNA
<213> ORGANISM: Artificial Sequence
<220> FEATURE:
<223> OTHER INFORMATION: Synthetic

<400> SEQUENCE: 63
caggaaacag ctatgacgaa agcaagcaag cttcacac                             38

<210> SEQ ID NO 64
<211> LENGTH: 37
<212> TYPE: DNA
<213> ORGANISM: Artificial Sequence
<220> FEATURE:
<223> OTHER INFORMATION: Synthetic

<400> SEQUENCE: 64
caggaaacag ctatgactgg tcgcacttat tttcctg                              37

<210> SEQ ID NO 65
<211> LENGTH: 37
<212> TYPE: DNA
<213> ORGANISM: Artificial Sequence
<220> FEATURE:
<223> OTHER INFORMATION: Synthetic

<400> SEQUENCE: 65
caggaaacag ctatgacagg gaacctggga gtagagg                              37

<210> SEQ ID NO 66
<211> LENGTH: 37
<212> TYPE: DNA
<213> ORGANISM: Artificial Sequence
<220> FEATURE:
<223> OTHER INFORMATION: Synthetic

<400> SEQUENCE: 66
caggaaacag ctatgacaac actgggttgt gggagag                              37

<210> SEQ ID NO 67
<211> LENGTH: 38
<212> TYPE: DNA
```

```
<213> ORGANISM: Artificial Sequence
<220> FEATURE:
<223> OTHER INFORMATION: Synthetic

<400> SEQUENCE: 67
tgtaaaacga cggccagtag acggcccaga ggagttag                                   38

<210> SEQ ID NO 68
<211> LENGTH: 37
<212> TYPE: DNA
<213> ORGANISM: Artificial Sequence
<220> FEATURE:
<223> OTHER INFORMATION: Synthetic

<400> SEQUENCE: 68
caggaaacag ctatgacctt cccttccttt cctccag                                    37
```

SCHWEINFURTHINS AND USES THEREOF

CROSS-REFERENCE TO RELATED APPLICATIONS

This patent application is a U.S. National Phase of International Patent Application No. PCT/US10/33153, filed Apr. 30, 2010, which claims the benefit of U.S. provisional patent application No. 61/174,338, filed Apr. 30, 2009, the disclosures of which are each incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 12,696 Byte ASCII (Text) file named "708971ST25.TXT," created on Sep. 22, 2011.

BACKGROUND OF THE INVENTION

Neurofibromatosis type 1 (NF1) is a common genetic disease affecting 1 in 3500 people, regardless of race or ethnicity. NF1 is characterized by a variety of benign lesions affecting many different organ systems, as well as an increased risk for several malignancies. NF1 is defined clinically by the presence of neurofibromas (benign tumors of peripheral nerves), cafe au lait patches (pigmented skin spots), Lisch nodules (iris hamartomas), optic pathway gliomas, abnormal bone development and impaired bone healing, cardiovascular problems such as heart valve and blood vessel abnormalities, as well as cognitive and learning disabilities. NF1 patients are at an increased risk for developing multiple tumor types, including malignant peripheral nerve sheath tumors, astrocytomas/glioblastomas, pheochromocytomas, and leukemia. Many of the common benign features of NF1, such as cafe au lait patches and neurofibromas, can be extremely disfiguring leading to a greatly reduced quality of life. Neurofibromas can also cause extreme pain that is very difficult to alleviate. The malignant tumors associated with NF1 are often incurable and the life expectancy for NF1 patients is significantly reduced compared to the general population. Many of these manifestations of NF1 affect very young children and require repeated and painful surgeries over the course of their childhoods and into adulthood. Because NF1 is common, results in increased mortality, results in decreased quality of life, and no treatments are currently available, there is an unmet need for the identification of a class of NF1-specific drugs for NF1 therapy.

BRIEF SUMMARY OF THE INVENTION

The invention provides, in one embodiment, a method for preventing or treating an undesirable condition in a subject carrying cells homozygous null for the neurofibromatosis type 1 gene (e.g., NF1−/−) or subjects that are haploinsufficient for the gene (e.g., NF1−/+), the method comprising administering to a subject in need thereof an effective amount of a schweinfurthin or schweinfurthin analog or derivative, or a pharmaceutically acceptable salt, prodrug, hydrate, or solvate thereof.

The invention also provides in another embodiment a compound or a pharmaceutical composition comprising such a compound and a pharmaceutically acceptable carrier, wherein the compound is a schweinfurthin or schweinfurthin analog or derivative, or a pharmaceutically acceptable salt, prodrug, hydrate, or solvate thereof, for preventing or treating an undesirable condition in a subject carrying cells homozygous null for the neurofibromatosis type 1 gene (e.g., NF1−/−) or subjects that are haploinsufficient for the gene (e.g., NF1−/+).

In another embodiment, the invention provides a compound of the formula

Formula I

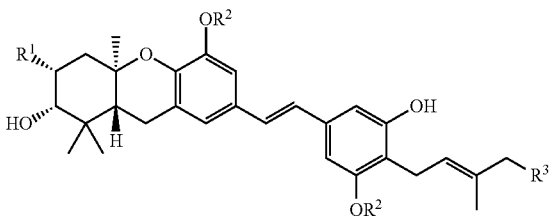

or a pharmaceutically acceptable salt, prodrug, hydrate, or solvate thereof.

In another embodiment, the invention provides a compound of the formula

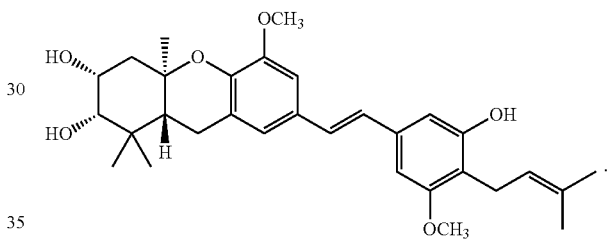

In another embodiment, the invention provides a compound of the formula

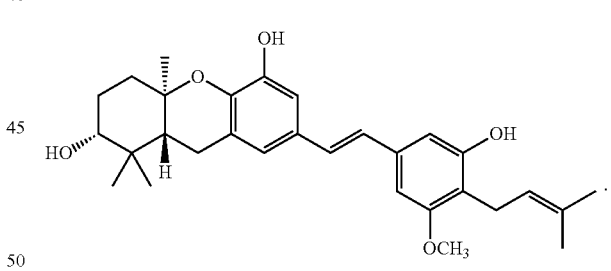

DETAILED DESCRIPTION OF THE INVENTION

Figure 1:
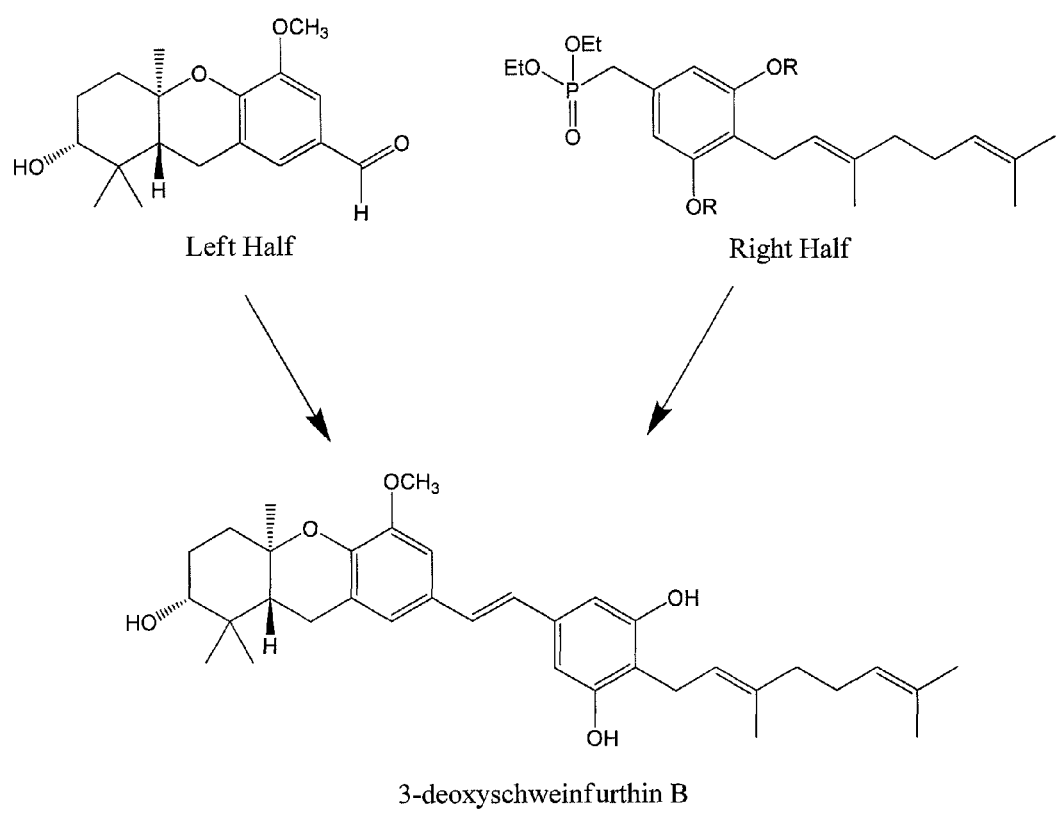
FIG. 1 shows an overall synthetic plan for schweinfurthins in accordance with an embodiment of the invention. Specifically shown is 3-deoxyschweinfurthin B.

The invention provides, in one embodiment, a method for preventing or treating an undesirable condition in a subject carrying cells homozygous null for the neurofibromatosis type 1 gene (e.g., NF1−/−) or subjects that are haploinsufficient for the gene (e.g., NF1−/+), the method comprising administering to a subject in need thereof an effective amount of a schweinfurthin or schweinfurthin analog or derivative, or a pharmaceutically acceptable salt, prodrug, hydrate, or solvate thereof with the proviso that the schweinfurthin or schweinfurthin analog or derivative is not schweinfurthin A. In another embodiment, the schweinfurthin or schweinfurthin analog or derivative is not 3dSB.

The invention also provides in another embodiment a compound or a pharmaceutical composition comprising such a compound and a pharmaceutically acceptable carrier, wherein the compound is a schweinfurthin or schweinfurthin analog or derivative, or a pharmaceutically acceptable salt, prodrug, hydrate, or solvate thereof, with the proviso that the schweinfurthin or schweinfurthin analog or derivative is not schweinfurthin A, for preventing or treating an undesirable condition in a subject carrying cells homozygous null for the neurofibromatosis type 1 gene (e.g., NF1−/−) or subjects that are haploinsufficient for the gene (NF1−/+). In another embodiment, the schweinfurthin or schweinfurthin analog or derivative is not 3dSB.

In another embodiment, the invention provides a compound of the formula

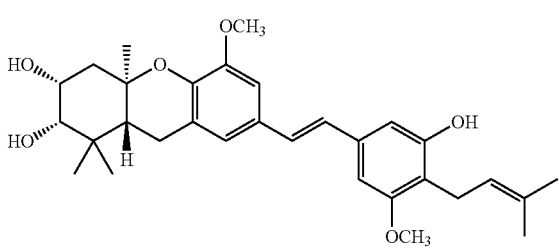

In another embodiment, the invention provides a compound of the formula

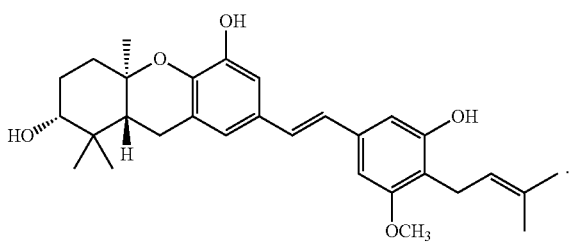 [SMILES: COc1cc(/C=C/c2cc(O)c3c(c2)C[C@@H]2C(C)(C)[C@H](O)CC[C@@]2(C)O3)cc(O)c1CC=C(C)C]

Schweinfurthins were originally isolated from an extract of the Cameroonian plant *Macaranga schweinfurthii* Pax. Schweinfurthin A ("SA") and B have significant differential cytotoxicity in the NCI 60-cell line panel. The central nervous system (CNS) cell lines and the leukemia cell lines showed particular sensitivity to schweinfurthins, with $IC_{50}$ values in the low nM range. SA is also a highly selective small molecule, showing 1000-fold selectivity. The cells most sensitive to SA are gliomas. The Cancer Gene Atlas (TCGA) project identified NF1 as one of the genes most frequently mutated in sporadic gliomas. U.S. Pat. No. 7,358,377 (incorporated by reference) describes the synthesis of 3-deoxyschweinfurthin B and related compounds.

In accordance with an embodiment of the invention, the schweinfurthins of the present invention include compounds of Formula I, or a pharmaceutically acceptable salt, prodrug, hydrate, or solvate thereof, with the proviso that when $R^1$ and $R^2$ are H, $R^3$ is not a $C_5$ alkenyl. Formula I is represented by:

Formula I

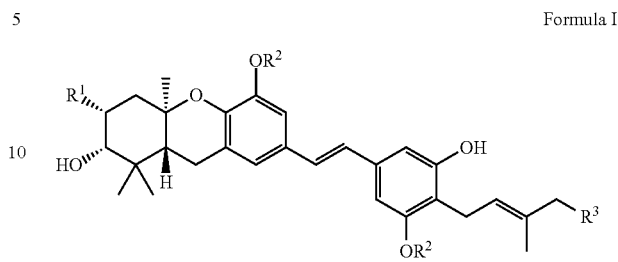

wherein $R^1$ may be H or hydroxyl, each $R^2$ may independently be H or alkyl, and $R^3$ may be H, alkyl, or alkenyl. In one embodiment, $R^1$ may be H or hydroxyl, each $R^2$ may independently be H or alkyl, and $R^3$ may be H, alkyl, or alkenyl with the proviso that when $R^1$ and $R^2$ are H, $R^3$ is not a $C_5$ alkenyl. The alkyl or alkenyl radicals may be straight chain or branched, the alkyl having 1-12 carbon atoms, preferably 1-6 carbon atoms, and the alkenyl having 2-12 carbon atoms, preferably 2-6 carbon atoms. Specifically, alkyl can be, e.g., methyl, ethyl, propyl, isopropyl, butyl, iso-butyl, sec-butyl, t-butyl, pentyl, 3-pentyl, etc.; alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, etc. Additionally, analogs of schweinfurthins are compounds of Formula I wherein any one of the oxygen atoms is replaced by a nitrogen or sulfur, e.g., isosteres of the compounds of Formula I and derivatives of schweinfurthins are compounds with a structure of Formula I with additional chemical groups attached to Formula I, such groups being, e.g., halo, hydroxyl, nitro, amino, haloalkyl, cyano, alkylamino, dialkylamino, formyl, alkylcarbonyl, alkylcarboxy, alkylcarbonyloxy, and the like on the aromatic ring or rings.

Table 1 shows specific structures of various schweinfurthins described herein.

TABLE 1

| Compound | Structure |
|---|---|
| Schweinfurthin A (SA) | 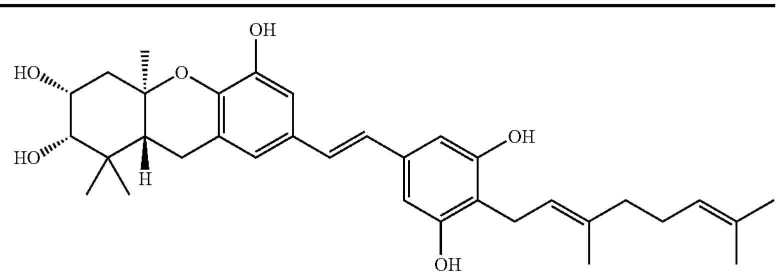 |
| Schweinfurthin B (SB) | 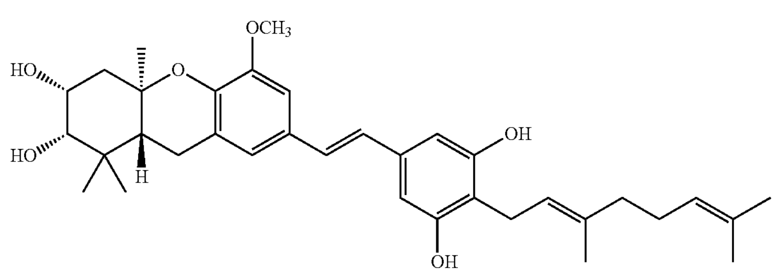 [SMILES: COc1cc(/C=C/c2cc(O)c(C/C=C(\C)CCC=C(C)C)c(O)c2)cc2c1O[C@]1(C)C[C@@H](O)[C@@H](O)C(C)(C)[C@H]1C2] |

TABLE 1-continued

| Compound | Structure |
|---|---|
| 3-Deoxyschweinfurthin B (3dSB) | 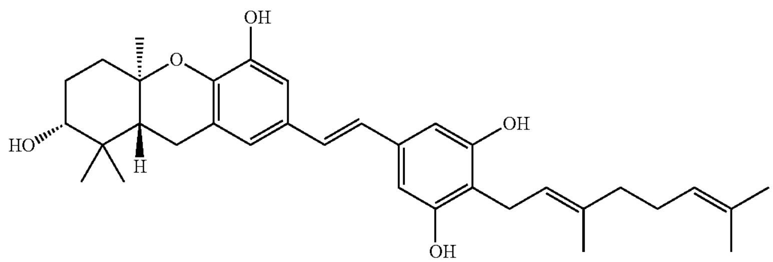 [SMILES: CC(C)=CCC/C(C)=C/Cc1c(O)cc(/C=C/c2cc(O)c3c(c2)C[C@@H]2C(C)(C)[C@H](O)CC[C@@]2(C)O3)cc1O] |
| 5'-Methylschweinfurthin E (5'MeSE) | 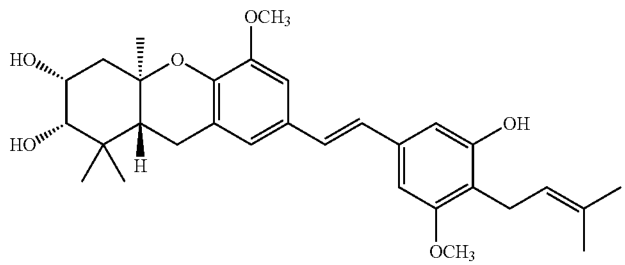 [SMILES: COc1cc(/C=C/c2cc3c(c(OC)c2)O[C@]2(C)C[C@@H](O)[C@@H](O)C(C)(C)[C@H]2C3)cc(O)c1CC=C(C)C] |
| 5'-Methylschweinfurthin G (5'MeSG) | 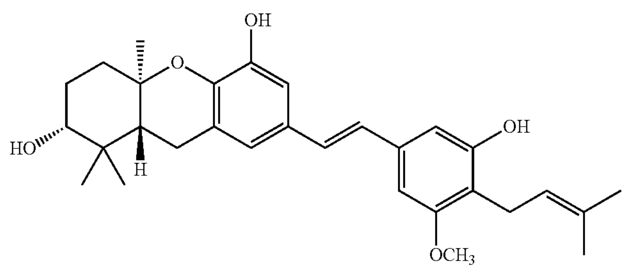 [SMILES: COc1cc(/C=C/c2cc(O)c3c(c2)C[C@@H]2C(C)(C)[C@H](O)CC[C@@]2(C)O3)cc(O)c1CC=C(C)C] |

A prodrug of a schweinfurthin is a compound which releases the schweinfurthin in the body. For example, any hydroxyl group may be converted to, e.g., an ester, amide, etc. Such prodrugs may be converted in the body, e.g., blood, or hydrolyzed, for example, in the acidic or alkaline conditions of the gastroenteric system. Also, schweinfurthins may be covalently attached to, for example, polyethylene glycol and/or saccharides (such as mono- and/or polysaccharides) using, e.g., a hydroxyl group on the schweinfurthin. For additional information on prodrugs, see Higuchi and Stella, Prodrugs as Novel Delivery Systems, 14 of the ACS Symposium Series, 14, 1975; Bundgaard, H., "Design of Bioreversible Drug Derivatives and the Utility of the Double Prodrug Concept" In Bioreversible Carriers in Drug Design; Roche, E. B., Ed.; Pergamon Press: New York, 1987, which are incorporated by reference.

A hydrate of a schweinfurthin is a schweinfurthin associated with a water molecule or molecules, such as 0.5, 1, 1.5, 2, 2.5, 3, or more water molecules per molecule of schweinfurthin. Such association may occur in the solid state upon crystallization of a schweinfurthin or upon lyophilization of a schweinfurthin.

A solvate of a schweinfurthin is a schweinfurthin associated with a solvent molecule. For example, a schweinfurthin may be dissolved in a solvent such as methanol, ethanol, acetone, acetonitrile, etc. Upon drying, the solid form of the compound may continue to be associated with molecules of the solvent.

Schweinfurthins are believed to be excellent compounds for the development of therapies for NF1 generally and for a variety of NF1-associated conditions. These conditions include manifestations due to the loss of the NF1 gene and the aberrant NF1 pathway, generally. Specific examples include tumors, including malignant peripheral nerve sheath tumors (MPNSTs), neurofibromas, pilocytic astrocytomas, anaplastic astrocytomas, glioblastomas (GBM), pheochromocytomas, rhabdomyosarcomas, and myeloid leukemia, particularly juvenile myelomonocytic leukemia (JMML). Schweinfurthin A shows activity at low concentrations, with a $GI_{50}$ value of 10 nM in Nf1-mutant astrocytoma cells, with no inhibition of Nf1 heterozygous cells at concentrations of 1 µM, providing a potential therapeutic window for the treatment of NF1 patients. This suggests that schweinfurthins could be used to treat any aspect of neurofibromatosis in which loss of heterozygosity or null mutation of the NF1 gene plays a decisive role. This could also include non-tumor disease manifestations, such as pseudarthrosis, vasculopathy, learning disabilities, among others.

"Homozygous null" is the deletion of both alleles of a gene or loss of function of both alleles of a gene, which may be due to complete removal of one or both alleles, mutation of one or both alleles, or removal of one and mutation of another. "Haploinsufficiency" occurs when one allele for a gene is deleted or mutated, and the remaining allele does not produce enough gene product to achieve function at a homozygous wild-type level.

The terms "individual" and "subject" are used interchangeably. Preferably, the subject is a mammal. The mammal can be any suitable mammal, such as a mammal selected from the group consisting of a mouse, rat, guinea pig, hamster, cat, dog, pig, cow, horse, and primate. The mammal preferably is a human, especially a human patient.

A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state or to determine the genotype of the individual.

Modulation of a cellular pathway is an altering, by increasing or decreasing, the activity of the pathway. Such activity modulation, e.g., may be achieved through altering of expression of a gene product (e.g., proteins, mRNA, etc.) within the pathway or direct interaction with a gene product of the pathway.

Without wishing to be bound by any theory, NF1 is caused by mutations in the NF1 gene that encodes the protein neurofibromin. Neurofibromin is over 2000 amino acids long with the only well-characterized function being attributed to a 300 aa domain in the middle of the protein that functions as a ras GTPase activating protein (rasGAP), which results in negative regulation of ras, functionally suppressing ras signaling in cells. When neurofibromin is absent or mutated, ras becomes hyperactivated and tumors can result. Evidence is accumulating that the phenotypes associated with NF1 loss depend on cytoskeletal regulators Rho and Rac, proteins that are also part of the ras superfamily. Specifically, loss of NF1 has been shown to result in excessive actin stress fiber accumulation dependent on RhoA signaling. Because neurofibromin has an important role in down-regulating ras, many cell types that are heterozygous (e.g., NF1−/+) have been found to be hypersensitive to growth factors, resulting in a haploinsufficient phenotype. Thus, in accordance with the invention, patients with a germline mutation in NF1 may respond differently to molecularly targeted therapies compared to normal individuals, due to altered signal transduction in cells throughout the body.

The schweinfurthin or schweinfurthin analog or derivative, or a pharmaceutically acceptable salt, prodrug, hydrate, or solvate thereof described herein may be administered using pharmaceutically acceptable carriers, for example, vehicles, adjuvants, excipients, or diluents, are well known to those who are skilled in the art and are readily available to the public. The pharmaceutically acceptable carrier can be any of those conventionally used and is limited only by chemico-physical or biological considerations, such as solubility and lack of reactivity with the schweinfurthin or schweinfurthin analog or derivative, or a pharmaceutically acceptable salt, prodrug, hydrate, or solvate thereof, lack of detrimental side effects or toxicity under the conditions of use, and route of administration. The choice of carrier will be determined in part by the particular form of schweinfurthin or schweinfurthin analog or derivative (e.g., any pharmaceutically acceptable salt, prodrug, hydrate, or solvate thereof). It will be appreciated by one of skill in the art that, in addition to the following described pharmaceutical compositions, the compounds of the present invention can be formulated as inclusion complexes, such as cyclodextrin inclusion complexes, or liposomes. Pharmaceutically acceptable carriers include, but are not limited to, USP water, saline, Cremophor EL (Sigma Chemical Co., St. Louis, Mo.), propylene glycol, polyethylene glycol, alcohol, and combinations thereof. There is a wide variety of suitable formulations of the composition. The pharmaceutical compositions may be administered as, for example, oral, aerosol, parenteral, subcutaneous, intravenous, intraarterial, intramuscular, interperitoneal, intrathecal, rectal, and vaginal formulations. Many methods are available for preparing liposomes, as described in, for example, Szoka et al., Arm. Rev. Biophys. Bioeng., 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Suitable carriers and their formulations are further described in A. R. Gennaro, ed., Remington: The Science and Practice of Pharmacy (19th ed.), Mack Publishing Company, Easton, Pa. (1995).

The schweinfurthins or schweinfurthin analogs or derivatives, or a pharmaceutically acceptable salt, prodrug, hydrate, or solvate thereof of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The schweinfurthin or schweinfurthin analog or derivative, or a pharmaceutically acceptable salt, prodrug, hydrate, or solvate thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The schweinfurthin or schweinfurthin analog or derivative, or a pharmaceutically acceptable salt, prodrug, hydrate, or solvate thereof may be made into injectable formulations. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986).

Additionally, the schweinfurthin or schweinfurthin analog or derivative, or a pharmaceutically acceptable salt, prodrug, hydrate, or solvate thereof may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The schweinfurthin or schweinfurthin analog or derivative, or a pharmaceutically acceptable salt, prodrug, hydrate, or solvate thereof or a composition thereof can also be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

Topical formulations, including those that are useful for transdermal drug release, are well known to those of skill in the art and are suitable in the context of embodiments of the invention for application to skin.

The concentration of schweinfurthin or schweinfurthin analog or derivative, or a pharmaceutically acceptable salt, prodrug, hydrate, or solvate thereof of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

The terms "treat," and "prevent" as well as words stemming therefrom, as used herein, do not necessarily imply 100% or complete treatment or prevention. For example, it can include 10, 20, 30, 40, 50, 60, 70, 80, or 90%. Rather, there are varying degrees of treatment or prevention of which one of ordinary skill in the art recognizes as having a potential benefit or therapeutic effect. In this respect, the inventive methods can provide any amount of any level of treatment or prevention of a condition associated with, e.g., tumors associated with NF1 or the peripheral nervous system. Furthermore, the treatment or prevention provided by the inventive method can include treatment or prevention of one or more conditions or symptoms of the disease being treated or prevented. Also, for purposes herein, "prevention" can encompass increasing longevity or delaying the onset of the disease, or a symptom or condition thereof, and includes, e.g., prevention of conversion of pre-malignant tissues to malignant tissues as well as preventing metastasis.

An "effective amount" refers to a dose that is adequate to prevent or treat a disease or condition, e.g., tumors associated with NF1 or the peripheral nervous system or non-tumor manifestations such as pseudarthrosis. Amounts effective for a therapeutic or prophylactic use will depend on, for example, the stage and severity of the condition, disease or disorder being treated, the age, weight, and general state of health of the patient, and the judgment of the prescribing physician. The size of the dose will also be determined by the schweinfurthin or schweinfurthin analog or derivative, or a pharmaceutically acceptable salt, prodrug, hydrate, or solvate thereof selected, method of administration, timing and frequency of administration as well as the existence, nature, and extent of any adverse side-effects that might accompany the administration of a particular schweinfurthin or schweinfurthin analog or derivative, or a pharmaceutically acceptable salt, prodrug, hydrate, or solvate thereof and the desired physiological effect. It will be appreciated by one of skill in the art that various conditions, diseases or disorders could require prolonged treatment involving multiple administrations, perhaps using a schweinfurthin or schweinfurthin analog or derivative, or a pharmaceutically acceptable salt, prodrug, hydrate, or solvate thereof in each or various rounds of administration. Typical doses might be, for example, 0.1 mg to 1 g daily, such as 5 mg to 500 mg daily. Non-limiting examples of doses may be, e.g., higher for treating an existing condition, disease or disorder and lower for preventing a condition, disease or disorder. For example, to treat an existing condition, disease or disorder, the dose may be 1 mg, 5 mg, 10 mg, 20 mg, 50 mg, 100 mg, 200 mg, 400 mg, 500 mg, or higher each day. For example, to prevent a condition, disease or disorder, the dose may be 0.01 mg, 0.1 mg, 0.5 mg, 1 mg, or higher each day.

Methods for preparing administrable (e.g., parenterally administrable) compositions are known or apparent to those skilled in the art and are described in more detail in, for example, Remington's Pharmaceutical Science (17th ed., Mack Publishing Company, Easton, Pa., 1985).

When a schweinfurthin or schweinfurthin analog or derivative, or a pharmaceutically acceptable salt, prodrug, hydrate, or solvate thereof is administered with one or more additional therapeutic agents, one or more additional therapeutic agents can be coadministered to the individual. By "coadministering" is meant administering one or more additional therapeutic agents and a schweinfurthin or schweinfurthin analog or derivative, or a pharmaceutically acceptable salt, prodrug, hydrate, or solvate thereof sufficiently close in time such that a schweinfurthin or schweinfurthin analog or derivative, or a pharmaceutically acceptable salt, prodrug, hydrate, or solvate thereof can enhance the effect of one or more additional therapeutic agents. In this regard, a schweinfurthin or schweinfurthin analog or derivative, or a pharmaceutically acceptable salt, prodrug, hydrate, or solvate thereof can be administered first and the one or more additional therapeutic agents can be administered second, or vice versa. Alternatively, a schweinfurthin or schweinfurthin analog or derivative, or a pharmaceutically acceptable salt, prodrug, hydrate, or solvate thereof and the one or more additional therapeutic agents can be administered simultaneously. Other compounds that may be coadministered with a schweinfurthin or schweinfurthin analog or derivative, or a pharmaceutically acceptable salt, prodrug, hydrate, or solvate thereof may include compounds that are anticancer agents and/or inhibit tumor growth, such as camptothecin or doxorubicin. Also, other compounds that inhibit the ras pathway may be coadministered.

The following examples further illustrate the invention but, of course, should not be construed as in any way limiting its scope.

Example 1

This example demonstrates a synthetic method for schweinfurthins by combining different right and left halves of the compound.

Synthesis of natural Schweinfurthins B, C, E, F, and G has been accomplished, as well as many synthetic derivatives. A total of 47 synthetic analogues of the natural schweinfurthins have been tested in a NCI 60 cell line assay, with 34 showing some selectivity. In addition, the (R,R,R)- and (S,S,S)-enantiomers of schweinfurthin F have been synthesized, which led to the identification of the (R,R,R)-enantiomer as the naturally occurring form. The synthetic strategy is based on constructing schweinfurthins as a phosphonate half and an aldehyde half (FIG. 1), which are then combined to assemble the stilbene olefin via a Horner-Wadsworth-Emmons condensation (Mente et al., J. Org. Chem., 2008, 73:796370; Neighbors et al., J. Org. Chem., 2005, 70:925-31, both incorporated by reference).

This approach allows the development of many analogs through a mix-and-match approach of combining different right and left halves. The synthesis of the Schweinfurthin B analog, 3-deoxyschweinfurthin B (FIG. 1), has been optimized to require just 10 steps, proceeds with about 32% overall yield, with more than 400 mg having been prepared. To improve the stability of the synthetic schweinfurthins, the D-ring has been modified to bear one hydroxy and one methoxy group (e.g., 5'-methylschweinfurthin E and 5'-methylschweinfurthin G). These compounds are comparably active with $GI_{50}$ values in the low nM range but appear to be more stable chemically than the free resorcinols.

Example 2

This example demonstrates the effect of schweinfurthins on NF1−/− cells and demonstrates schweinfurthins may act through a novel cellular mechanism.

Cell lines and culture: Human tumor lines SF-295 and A549 were obtained from the Developmental Therapeutics Program (NCI, Frederick, Md., USA) from stocks used in the NCI 60-cell assay. Mouse tumor lines were generated from NPcis mouse tumors (see below). The isolation of KR158 astrocytoma was described previously (Reilly et al., Nat. Genet., 2000, 26:109-13). K16561 and K14553 tumor lines were isolated from sarcomas in NPcis mice, and characterized as MPNSTs by immunocytochemistry (see below) for Schwann cell markers (S 100 and p75), which were found to be positive, and muscle markers (MyoD1 and Myf4) (Reilly et al., Cancer Res., 2006, 66:62-8), which were found to be negative, as well as for loss of the wt copy of Nf1 and Trp53 by PCR as described previously (Reilly et al., Nat. Genet., 2000, 26:109-13). Human cells were grown in RPMI 1640 and mouse cells were grown in DMEM containing 10% fetal bovine serum supplemented with 2 mmol/L glutamine and incubated in a 37° C. humidified atmosphere (5% $CO_2$).

Sequencing of NF1 and Protein Detection of Neurofibromin in SF-295 Cells: SF-295 total RNA was isolated from a 10 cm dish of confluent cells using Trizol Reagent (Invitrogen, Carlsbad, Calif., USA) and by following the manufacturer's protocol. The isolated total RNA was quantitated using a NanoDrop (NanoDrop Technologies, Wilmington, Del., USA). Prior to cDNA synthesis the total RNA was DNased-treated with DNAfree (Ambion, Austin, Tex., USA) following the manufacturer's protocol. cDNA was synthesized from 5 µg of total RNA using SuperScript First-Strand Synthesis System for RT-PCR (Invitrogen). SF-295 genomic DNA was isolated from a 10 cm dish of confluent cells by overnight digestion in 100 mM Tris, pH 8.5, 5 mM EDTA, 0.2% SDS, 200 mM NaCl, 400 ug/ml proteinase K. After digestion, the genomic DNA was precipitated, resuspended in $dH_2O$ and treated with two rounds of phenol/chloroform purification. Overlapping primer sets (SEQ ID NOS:1-16 as forward primers with SEQ ID NOS:17-32 as reverse primers, respectively) were designed to encompass the coding region of human neurofibromin 1 (NF1) mRNA (Accession NM_001042492). An additional primer set was also designed (SEQ ID NO: 33 as forward primer with SEQ ID NO: 34 as reverse primer) to amplify the 5' UTR and Exon 1 of Homo sapiens neurofibromin 1 (NF1) genomic DNA (Accession NG 009018). For each of the forward and reverse primers a M13 leader sequence was added to the 5' end to facilitate sequencing of the PCR products (SEQ ID NOS: 35-50 as forward primers with SEQ ID NOS: 51-66 as reverse primers, respectively, SEQ ID NOS: 35-66 showing the full primer sequences with M13; SEQ ID NO: 67 gives the 5' UTR and Exon 1 forward primer with M13 sequence, SEQ ID NO: 68 gives the 5' UTR and Exon 1 reverse primer with M13 sequence). PCR products were synthesized using Platinum Taq DNA Polymerase High Fidelity (Invitrogen) following the manufacturer's protocol. PCR products were gel purified using QIAquick Gel Extraction Kit (Qiagen, Valencia, Calif., USA). Sequences were assembled and aligned using Lasergene SeqMan Pro (DNASTAR, Madison, Wis., USA)

Western blotting for Neurofibromin expression: Centrifuge-cleared whole cell lysates, entirely processed on ice, were collected from KR158, SF-295 and A549 cell lines using lysis buffer (50 mM HEPES, 150 mM NaCl, 25 mM NaF, 1 mM EDTA, 1 mM EGTA, 10% glycerol, 1% Triton X-100, pH 7.5, to which was freshly added 1 mM PMSF, 10 ug/ml aprotinin, 5 ug/ml leupeptin, and 1 mM Na orthovanadate). After acrylamide gel separation, the bands were transferred to a PVDF membrane using standard protocol but omitting the buffer methanol to augment the transfer of high molecular weight bands (90 min., 75V) Blots were probed with rabbit polyclonal antibody to NF1, N-terminal (Santa Cruz Biotechnology, Santa Cruz, Calif., USA, sc-68, diluted 1:1000), using secondary goat anti-rabbit-HRP (Jackson ImmunoResearch Laboratories, Inc., West Grove, Pa., USA, 1:25,000) and anti-GAPDH (Advanced Immunochemicals, Inc., Long Beach, Calif., USA, 1:1000), using secondary goat anti-mouse-HRP (Jackson ImmunoResearch Laboratories, 1:25,000). Reactions were visualized using ECL Plus (Amersham/GE Healthcase, Piscataway, N.J., USA) and detected with a Syn Gene Bio Imager. The main NF1 sized at ~250 kD.

Establishment of NPcis MPNST cell lines: Mice were euthanized by $CO_2$ asphyxiation and tumors were dissected. The tumor volume was measured. The tumor was then cut in half, and ½ fixed in 4% PFA. The other half was rinsed, then cut into 24 pieces of approximately equal size. Each piece was diced with a razor blade and placed in 1 well of a 24 well plate, along with 625 µL of Triple Express (Gibco, Grand Island, N.Y., USA) and 5 µL of recombinant DNAse (Roche, Indianapolis, Ind., USA). Tumors were triturated, then incubated at 37° C. in a 5% $CO_2$ incubator for 2-5 hours, with an additional trituration halfway through incubation time. At the end of the incubation, tumor pieces were triturated again, and suspended cells were transferred to 1.5 mL eppendorf tubes. One mL of DMEM was added to each tube, and tubes were centrifuged at 4000 rpm for 10 min. Media was removed from the pellet and discarded. The cell pellet was resuspended in 1 mL DMEM and plated in a new 24 well plate. After 24-72 hours of incubation, media containing non-adherent cells was transferred to a second 24 well plate, and adherent cells were fed with new DMEM. Both plates were monitored for cell growth, grown up to 10 cm plates, and frozen down in 10% DMSO. DNA, RNA and protein lysates were collected for further characterization.

MPNST characterization by PCR and Immunocytochemistry: Two cell lines, JW3 and JW6, were used in these experiments. JW3 was derived from a sarcoma in mouse K14553, and JW6 from a sarcoma in mouse K16561. DNA was genotyped for Nf1 and p53 as described previously (Reilly et al., Nat. Genet., 2000, 26:109-13) to confirm loss of heterozygosity. Immunocytochemistry was performed to determine expression of MPNST and rhabdomyosarcoma markers. Cells were plated on 22 mm coverslips in 6 well plates. Cells were grown to 50-70% confluence, then fixed in 4% PFA, washed 3× in PBS, and stored in PBS. Cells were permeabilized in 0.2% Triton-X for 15 min, then rinsed 3× in PBS. Cells were blocked for 1 hour in 5% Normal Goat Serum (Jackson ImmunoResearch, West Grove, Pa., USA) with 0.01% Tween-20. Cells were stained overnight at 4° in 1:100 Rabbit anti-mouse p75 NGF receptor AB1554 (Chemicon, Temecula, Calif., USA), 1:1000 Rabbit anti-cow 5100 (Dako, Carpinteria, Calif., USA), 1:50 mouse anti-MyoD1 clone 5.8A (Dako), and 1:30 Mouse AB 1554 anti-Myf4 (Novocastra, Newcastle upon Tyne, United Kingdom). Cells were incubated with 1:400 Alexa Fluor 488 Goat anti-rabbit IgG Invitrogen, or Alexa Fluor 488 Goat anti-Mouse (Invitrogen, Carlsbad, Calif., USA), respectively, along with 1:5000-1:8000 DAPI and 1:2000 Texas Red-phalloidin (both from Molecular Probes/Invitrogen). Cells were mounted in Vectashield Slides and examined with a Nikon Eclipse E6000, and photographed at 40× magnification using SPOT 3.5.9 for MacOSX. Times for each wavelength were kept consistent for each antibody being tested. For S100 staining, S100 exposure time was 250 ms, phalloidin was 1000 ms, and DAPI was 50 ms. For p75 staining, exposure times were 250 ms for p75, 500 ms for phalloidin, and 15 ms for DAPI. For MyoD1 and Myf4 staining, times were 2000 ms for MyoD1 and Myf4, and 500 ms for phalloidin. The RD cell line, derived from a human rhabdomyosarcoma (obtained from NIH, Bethesda, Md., USA) was used as a positive control for MyoD1 and Myf4. MEFs were used as a negative control for S100 expression.

All mouse procedures were performed according to the guidelines of the NCIFrederick Animal Care and Use Committee.

Clonogenic Assays: Monolayers of cells were treated for 18 hrs with SA, and then harvested, counted, and seeded to 35 mm dishes at a density of 1000 cells per dish. After one week, macroscopic colonies were stained with crystal violet (Sigma, St. Louis, Mo., USA) and counted.

XTT Cell Proliferation Assay: Cells were seeded into 96-well plates at a density of 2,000 cells/well and allowed to reattach overnight. Cells were treated with SA, synthetic analogs, camptothecin (NCI Chemotherapeutics Repository, Md., USA), or DMSO control at the indicated concentrations continuously for 48 hours followed by assay in the 96-well plate for relative viable cell number using the dye 3-(4,5-dimethylthiazol-2-yl)-2,5-diphenyltetrazolium bromide (XTT) and a Wallac-Victor 2 plate reader (Perkin-Elmer, Waltham, Mass., USA). Absorbance was determined at 450 nm with 650 nm as a reference reading. Primary astrocytes were additionally assayed at a 96 hour time point.

Cytotoxicity Assay: The MultiTox-Fluor Multiplex Cytotoxicity Assay (Promega, Madison, Wis., USA) was used according to manufacturer instructions. Briefly, KR158 cells were harvested and seeded 2,500 cells/well in a black walled 96-well plate (Corning, Lowell, Mass., USA). Cells were treated with SA or DMSO control at the indicated concentrations continuously for 48 hours followed by addition of the fluorescent substrates from the assay kit. The GF-AFC Substrate enters live cells where it is cleaved by the live-cell protease to release AFC. The bis-AAF-R110 substrate cannot enter live cells but instead is be cleaved by the dead-cell protease activity to release R110.

Figure 2A:
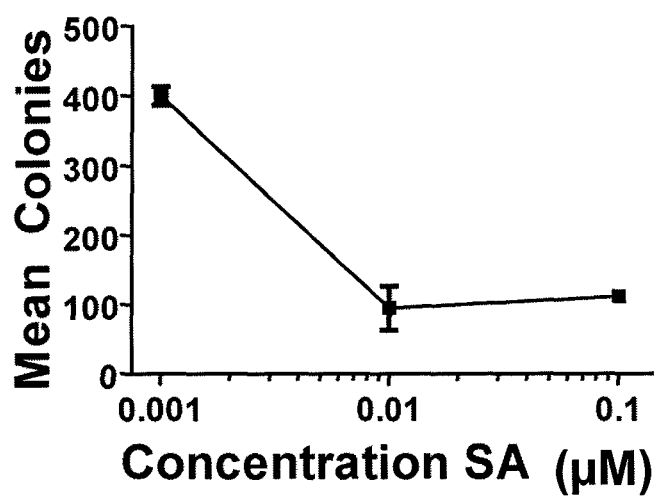
FIG. 2A shows a line graph of mean number of human central nervous system (CNS) tumor (SF-295) cells from three dishes each (error bars are sample standard deviations) as evaluated by growth of crystal violet-stained colonies. In accordance with an embodiment of the invention, this figure shows clonal growth of SF-295 human glioma cells is inhibited by schweinfurthin A (SA).
Figure 2B:
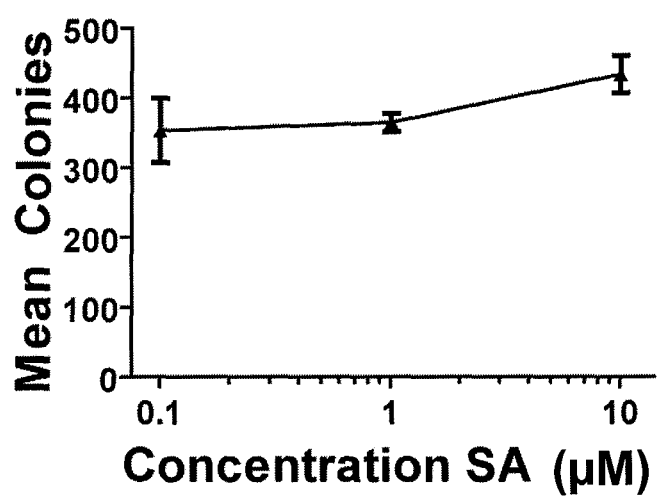
FIG. 2B shows a line graph of mean number of A549 clones from three dishes each (error bars are sample standard deviations) as evaluated by growth of crystal violet-stained colonies. In accordance with an embodiment of the invention, this figure shows growth of A549 human lung carcinoma cells is not inhibited after single administration of varying doses of SA.
Figure 3:
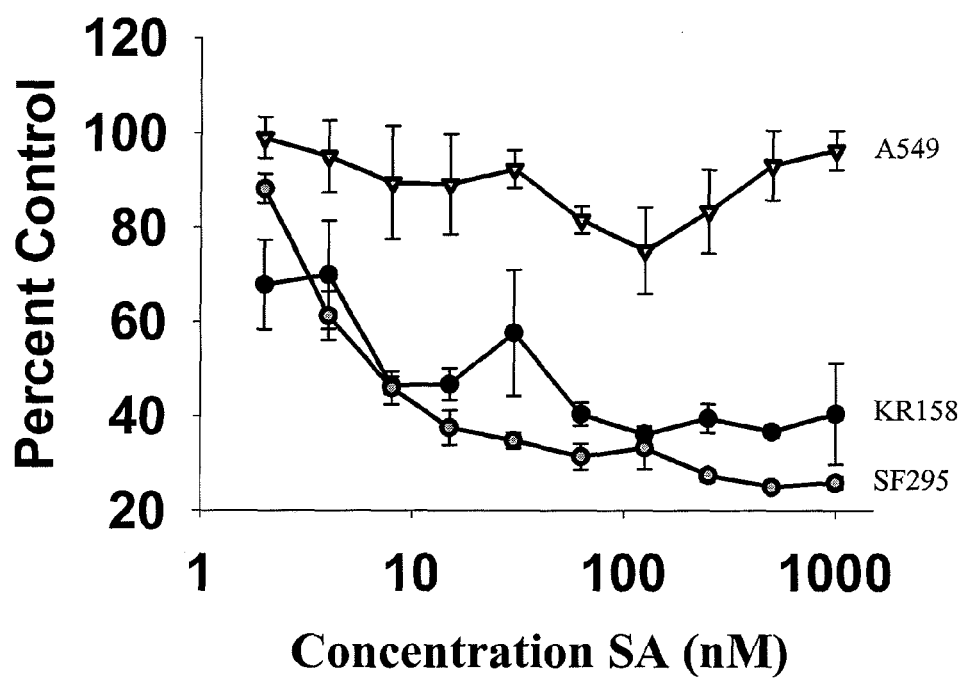
FIG. 3 is a line graph showing the sensitivity (percent viability versus control) of SF-295 cells, a mouse CNS tumor (KR158, which is Nf1−/−; Trp53−/−) cells, and A549 cells at increasing concentrations of SA. In accordance with an embodiment of the invention, this figure shows SA selectively inhibits clonogenicity of glioma cells.
Figure 4:
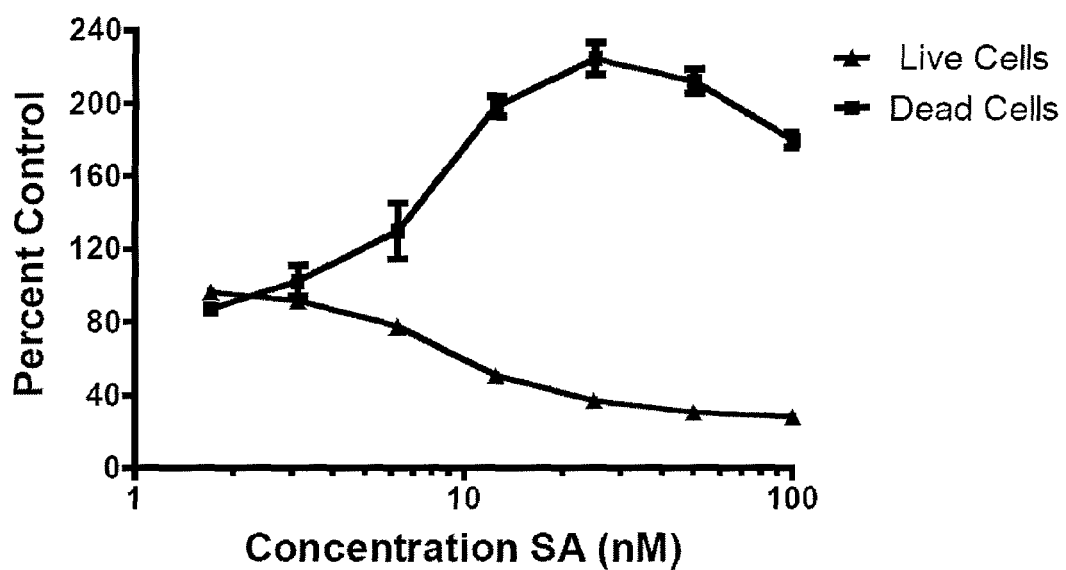
FIG. 4 is a line graph showing a live vs. dead cell assay at varying SA concentrations. Data is plotted as a percentage of cells treated with vehicle only (control). Data points are mean percentage growth of three wells compared to DMSO treated controls. In accordance with an embodiment of the invention, this figure shows that KR158 cells treated with SA show a dose dependent increase of dead-cell protease activity.

Schweinfurthin A shows differential activity towards SF-295 human glioma and KR158 astrocytoma cells but not primary astrocytes derived from wt, Nf1−/+, and NPcis mice. To confirm the selectivity of SA seen in the NCI 60 assay, a cell clonogenicity study was used in which confluent monolayers of SF-295 GBM cells were treated for 18 hours with SA. A549 lung cancer cells were used as a control for comparison, because they demonstrate relative resistance to SA compared to brain tumor lines in the NCI-60 cancer cell assay. SA-treated cells were then rescued from the drug, harvested, and seeded at low densities. As seen in FIG. 2, colony growth was dramatically restricted in the sensitive cells, while the A549 cells formed colonies up to the highest concentration of SA tested. The activity of SA was further characterized in an aggressive grade III astrocytoma cell line (KR158) derived from the NPcis mouse. The human GBM line SF-295 and the mouse astrocytoma line KR158 were compared to the SA resistant A549 lung cancer cell line in two-day proliferation assays. SA inhibited both the KR158 and SF-295 cell lines in a dose dependent manner, with no apparent effect on the A549 cell line (FIG. 3). The XTT assay used in these experiments measures the metabolic activity of mitochondrial associated enzymes that are inactivated after cell death, and is a validated endpoint for measuring inhibition of proliferation. However, because it does not measure cytotoxicity directly, a cell protease assay was employed that measures cell viability and cytotoxicity by detecting two distinct protease activities simultaneously. In this assay, a dose dependent increase in cell killing in KR158 cells was seen after 48 hrs of continuous treatment with SA (FIG. 4), indicating that SA acts by a cytotoxic rather than cytostatic mechanism.

Figure 5:
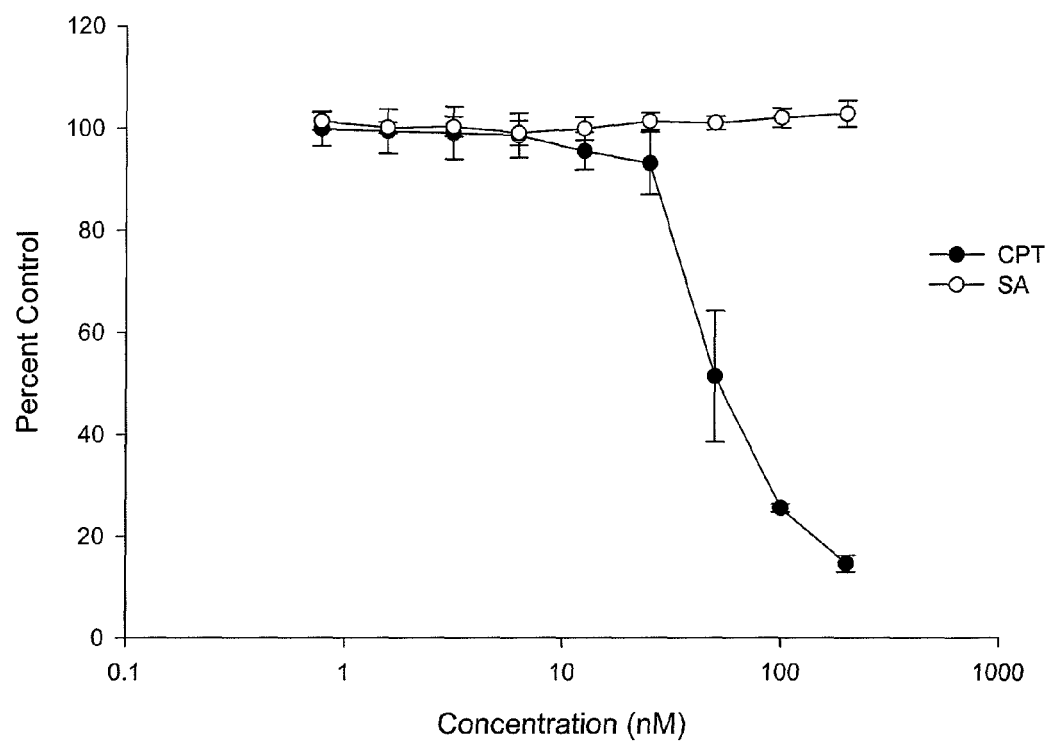
FIG. 5 is a line graph showing percent viability versus control of A549 cells in the presence of camptothecin (CPT) or SA at increasing concentrations. In accordance with an embodiment of the invention, this figure also shows SA selectively inhibits proliferation of SF-295 and KR158 brain tumor cells, in that it does not inhibit lung tumor cells.
Figure 6:
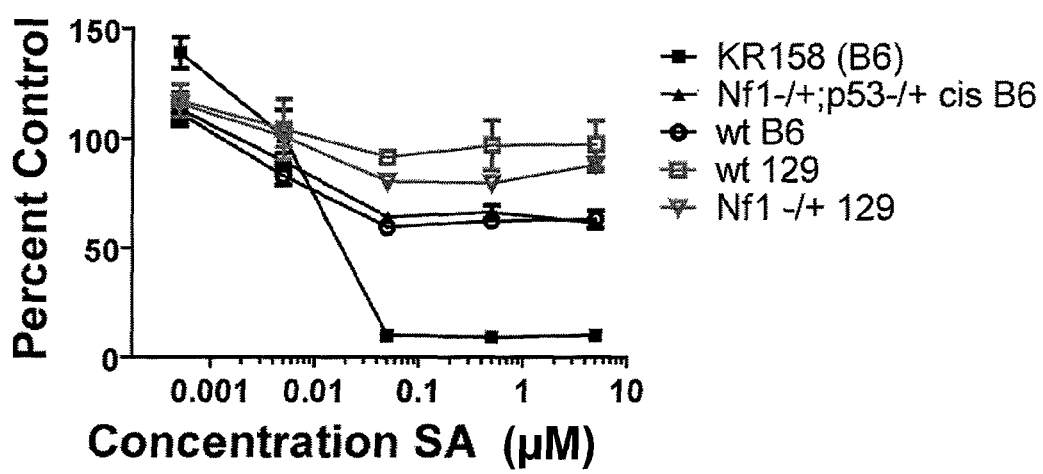
FIG. 6 is a line graph showing the viability of KR158 cells and four primary astrocyte cultures established from wt, Nf1−/+, or NPcis mice in response to SA as measured by XTT assay. Points are mean percentage growth of three wells. In accordance with an embodiment of the invention, this figure also shows SA selectively inhibits proliferation of SF-295 and KR158 brain tumor cells, in that it does not inhibit non-tumor astrocytes.
Figure 7:
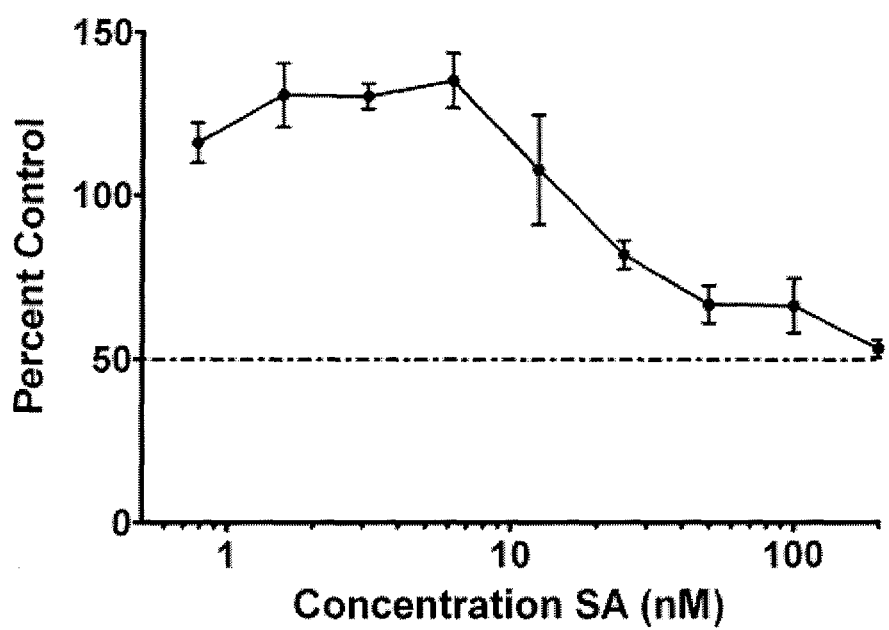
FIG. 7 is a line graph showing primary astrocyte cell line proliferation as evaluated by XTT assay after 96 hrs continuous treatment with the indicated concentrations of SA. Points are mean percentage growth of 6 wells compared to DMSO-treated controls. Dashed line indicates 50% of controls. In accordance with an embodiment of the invention, this figure shows mouse primary astrocytes are resistant to SA.
Figure 8:
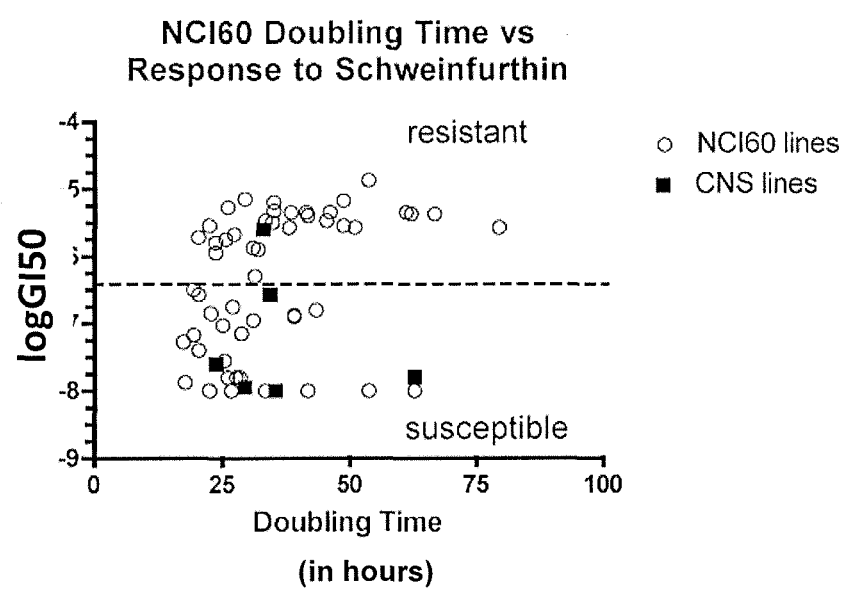
FIG. 8 is a dot graph showing the log of the $GI_{50}$ value plotted against the doubling time in hours of certain tested cell lines. All NCI60 cell lines are plotted as open circles, with CNS lines plotted as black boxes. In accordance with an embodiment of the invention, this figure shows the response of the NCI60 cell lines to SA does not correlate with the rate of growth of the individual cell lines.

To show that A549 cells are not generally resistant to small molecule growth inhibition, camptothecin (CPT), an inhibitor of topoisomerase 1 that induces apoptosis in proliferating cells, was tested as a positive control. A549 was sensitive to CPT, indicating that general upregulated drug metabolism, or increased non-specific drug efflux, were not responsible for enhancing the SA-insensitive tumor cell survival in the presence of the drug (FIG. 5). Furthermore, untransformed astrocytes have the capacity to proliferate; therefore SA was tested against primary astrocytes from wt, Nf1−/+, and NPcis neonates. It was found that these cells were resistant to the effects of SA on proliferation (FIG. 6), even after 96 hours of treatment (FIG. 7). Even at concentrations of SA several log-fold higher than the $GI_{50}$ value for KR158, primary astrocytes were not inhibited more than roughly 40% in their growth, depending of the individual astrocyte line tested. Because primary astrocytes grow slower than tumor cells, it is possible that the effects of SA are limited to faster proliferating cells. To address this issue, the response of the NCI60 cell lines to SA was examined. The doubling times of the NCI60 cells are well characterized. The sensitivity to SA does not correlate to the doubling time of the tumor line (FIG. 8). Indeed, one of the slowest growing CNS lines, SNB-75 with a doubling time of 62.8 hours, is one of the most sensitive lines to SA (logGI50=−7.82), whereas one of the faster growing CNS lines, SF-268 with a doubling time of 33.1 hours, is the most resistant CNS line to SA (logGI50=−5.62). These data suggest that SA activity targets the transformed phenotype of astrocytoma cells, and not a general feature of cell division that can be found in proliferating brain cells.

Using the COMPARE program (Keskin et al., Anticancer Drug Des., 2000, 15:79-98) it was found that schweinfurthins appear to have a novel mode of action and may represent a new pharmacophore.

Example 3

This example demonstrates cytoskeletal changes in the presence of schweinfurthins.

The cell culture methods of Example 2 were used in addition to the methods detailed below.

Cell culture: Primary astrocytes were prepared as described previously (Hawes et al., J. Biomol. Screen, 2008, 13:795-803) from 1 day old neonatal brains collected from wt, Nf1−/+, and Nf1−/+; Trp53−/+ cis mice.

Constructs and Transfections: NF1-GRD retroviral constructs were obtained from Indiana University. Cells transduced with the NF1-GRD construct or PMSCV empty vector control as previously described (Hiatt et al., J. Biol. Chem., 2001, 276:7240-5) were maintained in 1 μg/mL puromycin (Sigma).

Generation of Stable EGFP-Actin Expressing KR158 Cells for Live Cell Imaging: Because the KR158 cell line carries a neomycin resistance marker, a zeocin resistance cassette was inserted into pEGFP-Actin (BD Biosciences, San Jose, Calif., USA, cat#6116-1) in order to produce a stably transfected KR158/pEGFP-Actin cell line. The zeocin cassette was PCR-amplified from the AP-5Tag plasmid (obtained from NCI, Frederick, Md., USA) using primers containing Stu I restriction sites (Sense: 5'-gcg cgc agg cct tgt tga caa tta atc atc ggc-3' (SEQ ID NO: 1) and Anti-Sense: 5'-gcg cgc agg cct tca gtc ctg ctc ctc ggc cac-3' (SEQ ID NO: 2)). The PCR product was restriction digested and ligated into pEGFP-Actin. Positive clones were screened by restriction digestion for the presence of the inserted cassette. KR158 cells stably transfected with GFP-actin were supplemented with 10 μg/mL of Zeocin (Invitrogen, Carlsbad, Calif., USA).

Doxorubicin studies: KR158 stably transfected with GFP-actin were treated with 25 and 50 μM doxorubicin for 18 hrs continuously.

Cell Morphology Assays and Confocal Microscopy: To assay cytoskeleton morphology, KR158 cells, mouse primary astrocytes, KR158 clones expressing the NF1-GRD constructs, K14553 cells, and A549 were seeded to cover slips and allowed to reattach overnight. Cells were treated for 18 hours with either the indicated concentrations of SA, or the vehicle control DMSO. The cover slips were fixed in 3.7% paraformaldehyde, permeablized in 0.1% Triton-X100, and stained with Alexa Fluor 488-phalloidin (Invitrogen, Carlsbad, Calif., USA) to detect actin and cells were mounted in Prolong Antifade containing DAPI (Invitrogen) to stain nuclei. The cells were imaged on a LSM510 confocal microscope (Carl Zeiss Inc., Jena, Germany). For phospho-myosin light chain 2 (MLC) detection, cells were seeded to coverslips as described above. Cells were serum starved in 0.5% FBS and SA or DMSO vehicle control for 18 hours, and then pulsed with 10 ng/mL EGF (Invitrogen) for 5 min. Cover slips were fixed and permeablized as described above and immunostained with a Ser19 phopho-specific MLC primary antibody (Cell Signaling Technology, Danvers, Mass., USA, cat#3671S) and Alexa Fluor 555 Goat Anti Rabbit secondary (Invitrogen), and counterstained with Alexa Fluor 488-phalloidin (Invitrogen) to detect actin. Cells were mounted in Prolong Gold Antifade reagent containing DAPI (Invitrogen) to stain nuclei. KR158 GFP-actin transfected cells were seeded to 8-well chamber slides, allowed to reattach, and then treated with indicated concentrations of SA. Actin structures were monitored continuously over a 16 hr period using confocal microscopy equipped with a growth chamber (37° C., humidified atmosphere and 5% $CO_2$). To compare SA to Rho/Rock inhibitors, KR158 GFP-actin cells were treated with SA or with the Rho pathway inhibitors Rock inhibitor Y-27632 (Sigma, St. Louis, Mo., USA), and the Rho inhibitor C3 transferase (Cytoskeleton, Inc., Denver, Colo., USA, cat# CT04) for 16 hrs, and then examined by confocal microscopy.

Schweinfurthin A causes morphological changes reflected in alterations of dynamic actin architecture. Treatment of sensitive cells with SA leads to changes in cell morphology characterized by elongated processes and contraction of the cytoplasm, resulting in an overall spindle shape. These changes occur within the first day of treatment with the most dramatic changes occurring after 12-18 hrs. Hypothesizing that changes in the actin cytoskeleton were responsible for the morphological changes, KR158 cells stably transfected with GFP-actin were separately treated with the Rock inhibitor Y-27632 or the Rho inhibitor C3 transferase, both of which are known to disrupt cytoskeletal actin structures, or with SA. When compared to untreated controls, there was a dramatic loss of F-actin staining in all treated cells—especially stress fibers. In SA treated cells in particular, dose- and time-dependent changes were seen in the architecture of actin including loss of stress fibers, and increased cortical actin at the margins of the cell, 1. Distinctively, doxorubicin treated KR158 cells retained stress fibers when given cytotoxic doses of the DNA intercalating agent, suggesting that actin structure reorganization is not a general consequence of cell stress. Finally, SA resistant primary astrocytes and A549 cells showed no visible changes in actin organization after treatment with SA as visualized by phalloidin staining.

Example 4

This Example demonstrates schweinfurthin action on Rho-dependent pathways.

The general methods of Example 2 and Example 3 were used in addition to the methods detailed below.

Rho GTPase Pull-Down Assay: The Rho pull down assay was obtained from Upstate Biolotech/Millipore (Billerica, Mass., USA, Cat#17-294). KR158 cells were harvested at approximately 80% confluency and seeded at $5 \times 10^5$ cells per well in a 6-well plate. After overnight recovery, cells were serum starved in 0.5% FBS for 18 hrs. Cells were then treated with 10 ng/mL EGF either in the presence or the absence of the indicted concentrations of SA for up to 18 hours. At the indicated time points, the cells were lysed according to the manufacturer's protocols. Proteins pulled down by the Rho-GTP binding beads were eluted by SDS, fractionated on a 10% SDS-PAGE gel, and transferred to a nitrocellulose membrane. Pre-pull-down lysates were run in parallel to determine total levels of Rho in each sample. The membrane was probed by an anti Rho antibody.

Schweinfurthin A inhibits Growth Factor-Induced Rho signaling. To test whether SA might be targeting the Rho signaling network, KR158 cells were serum starved and then pulsed with 10 ng/mL of EGF in the presence or absence of SA. Using GST-fused Rhotekin-Rho binding domain to pull down activated Rho, a marked inhibition of Rho activity was observed at 12 hrs and 18 hrs in EGF pulsed cells treated with SA. As further evidence that the Rho signaling pathway is disrupted, KR158 cells treated with SA and EGF were immunostained for phosphorylation of Ser 19 on myosin light chain 2 (MLC2), which is downstream of Rho/Rock signaling. Ser 19 phosphorylation has been shown to activate the regulatory function of MLC, and is associated with stress fiber polymerization and contractility in the actin cytoskeleton. Confocal micrographs of these cells show a dose dependent decrease of MLC phosphorylation in SA treated cells. Taken together, these data suggest that the observed cytoskeletal changes in SA sensitive cells are due to the inhibition of Rho activity, with downstream consequences on Rho effector molecules such as MLC. Because the time course of the experiments show that the effects on the actin cytoskeleton, MLC phosphorylation and Rho activity require hours of treatment with SA, it is not likely that SA is acting directly within the Rho pathway, but rather it is acting upstream, indirectly leading to downregulation of the pathway. These data also suggest loss of neurofibromin contributes to the upregulation of a signaling network that links the regulation of the actin cytoskeleton and cell survival, and that this upregulated network in Nf1 deficient cells is targeted by SA. This data shows that SA functionally replaces Nf1 activity in Nf1 null cells by inhibiting EGF mediated Rho activation.

Example 5

This example further demonstrates the effect of schweinfurthins on NF1 cells.

The general methods of Examples 2, 3, and 4 were used in addition to the methods detailed below.

Cell lines and culture: Human MPNST cell lines (STS26T and T265) were obtained from the Pediatric Oncology Branch, NCI (Bethesda, Md., USA).

Western Blotting: NF1-GRD clones of KR158 were harvested at 80% confluency and seeded at a cell density of $5 \times 10^5$ cells/well in a 6-well plate, and allowed to recover overnight. Cells were then lysed in cold lysis buffer (Cell Signaling, Danvers, Mass., USA) containing a protease inhibitor cocktail. Lysates were clarified (10,000 rpm×15 mins), and then their protein concentrations were determined by BCA assay (Pierce, Rockford, Ill., USA). Equal amounts of protein were loaded to a SDS-PAGE gel, and proteins were fractionated. The proteins in the gel were transferred to a PDVF membrane. Equal loading, and transfer success were confirmed by Ponceau staining. The membrane was blocked and then probed overnight with the KT3 antibody to detect the NF1-GRD transgene product. Rabbit HRP was used as a secondary, and the bands were developed by chemiluminescence. Membranes were stripped and reprobed.

Figure 9:
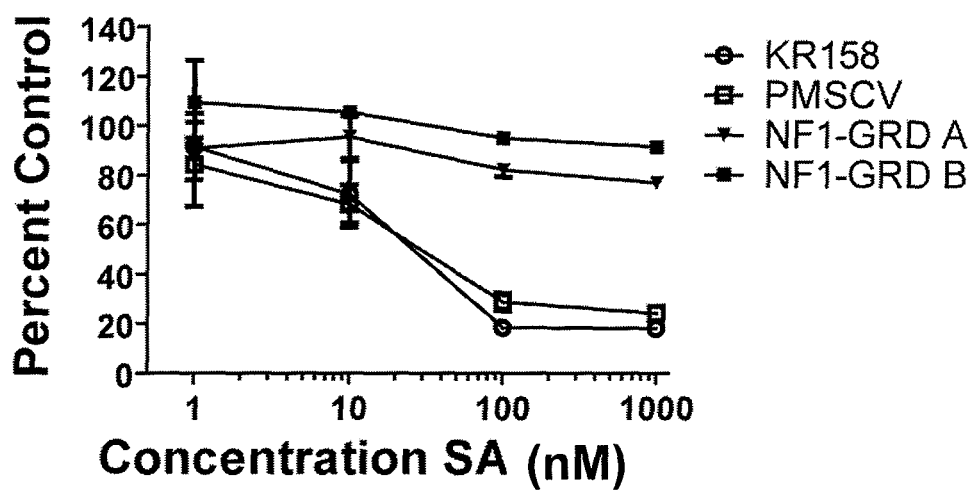
FIG. 9 is a line graph showing KR158 cells, KR158 cells transduced with empty vector (PMSCV), and KR158 cells stably transduced with the NF1-GRD domain at varying concentrations of SA, as measured by an XTT assay. Points are mean percentage growth of three wells compared to DMSO treated controls. In accordance with an embodiment of the invention, this figure shows SA activity is abrogated in Nf1 deficient cells by expression of the NF1-GRD domain.

KR158 cells transfected with the NF1-GRD domain are resistant to Schweinfurthin A. Because neurofibromin is a very large protein, stably transfecting cells with the full-length Nf1 gene was not feasible. Therefore, to test whether loss of Nf1 was required for cellular sensitivity to SA, the ~300 amino acid long NF1-GRD fragment of Nf1 was reintroduced into KR158 cells. While neurofibromin may have additional functions not mediated by this domain, this is a key fragment of the larger protein. Cells transduced with this domain, or the empty vector, were tested against SA in a two-day cell proliferation assay. As expected, SA was highly active against both the untransduced and the empty vector transduced KR158 cells; however, NF1-GRD expressing cells were resistant to SA inhibition (FIG. 9). Sequencing of the coding sequence corresponding to the first 1984 amino acids of neurofibromin in SF295 cells revealed 1 silent mutation in the N-term end of the protein (Leu234CTG>CTA), while Western blots of SF-295 and A549 for neurofibromin showed a 250 KD reactive band consistent with expression of neurofibromin in these cell lines. The neurofibromin expressed in SF295 (or A549) may not be functional; however no clear evidence for a mutation of NF1 in SF295 that would alter protein function was found. Therefore, the evidence suggests that SA targets a pathway critical for survival of NF1 null cells, but that this pathway could also be important for the survival of other nervous system tumors that may still express neurofibromin, but use similar pathways for tumorigenesis. Examination of the transduced cells by confocal microscopy showed that the NF1-GRD expressing clones had a different pattern of F-actin organization from the empty vector transduced cells, and the actin structures within the NF1-GRD cells did not change in response to SA. The empty vector transduced cells showed the same reorganization of F-actin structures in response to SA that was observed in untransduced KR158 cells and other sensitive cells lines tested.

Figure 10:
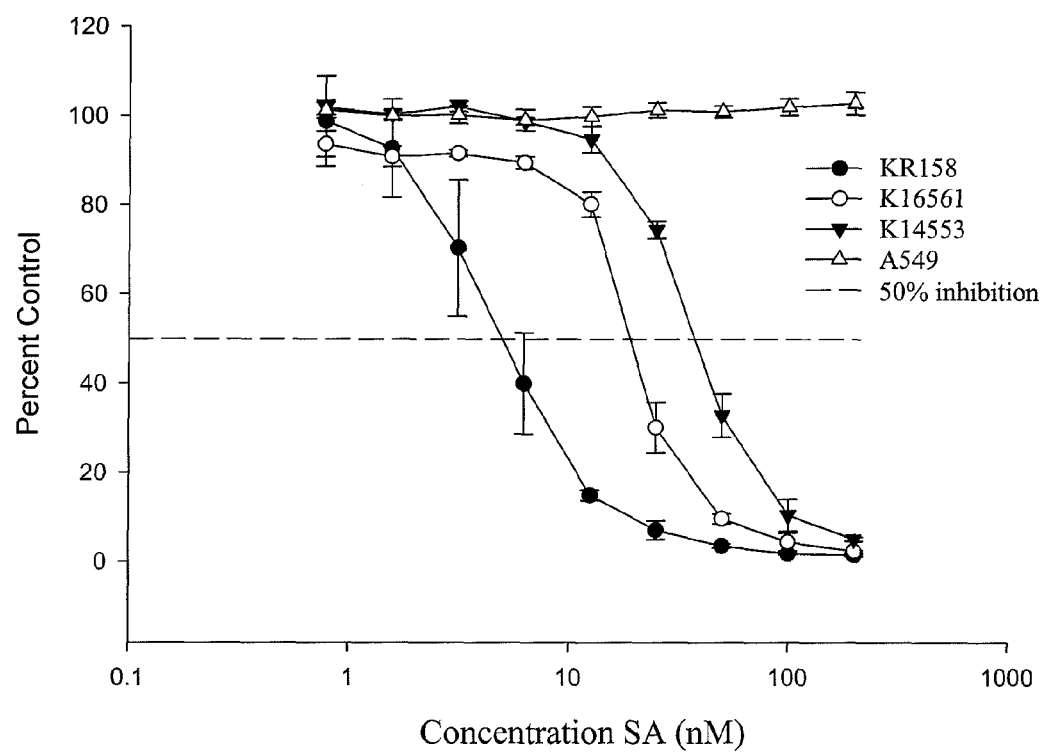
FIG. 10 is a line graph showing percent viability versus control of KR158, mouse malignant peripheral nerve sheath tumor (MPNST) K16561, mouse MPNST K14553, and human A549 cells at increasing concentrations of SA. In accordance with an embodiment of the invention, this figure shows that KR158 cells, K16561 cells, and K14553 cells are sensitive to SA, whereas A549 cells are not.
Figure 11:
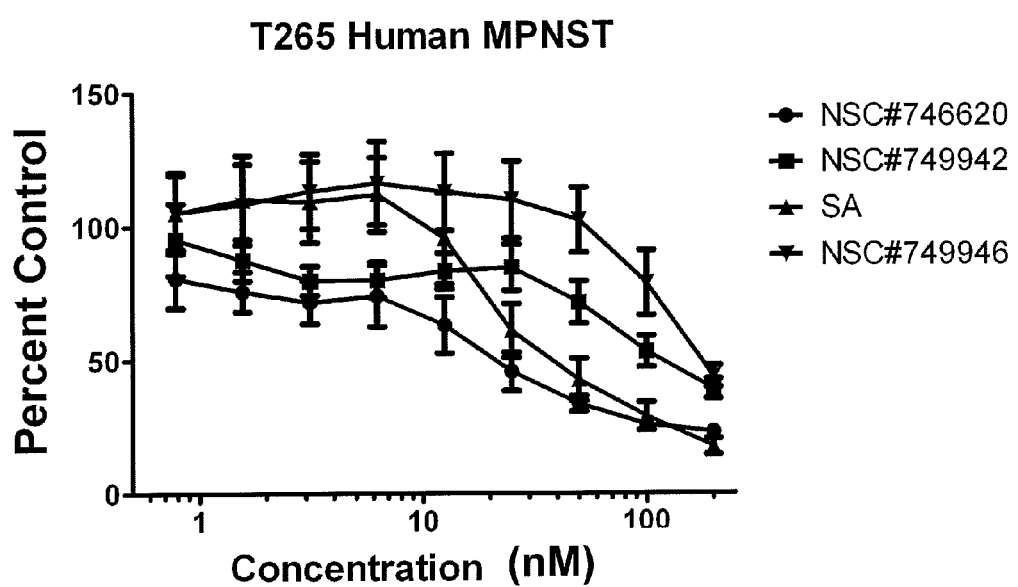
FIG. 11 is a line graph showing percent viability versus control of human MPNST T265 cells at increasing concentrations of various schweinfurthins. NSC#746620 is 5′-methylschweinfurthin G (5′MeSG), NSC#749946 is schweinfurthin B (SB), and NSC#749942 is 5′-methylschweinfurthin E (5′MeSE). In accordance with an embodiment of the invention, this figure shows T265 cells are sensitive to SA and synthetic analogs of SA.
Figure 12:
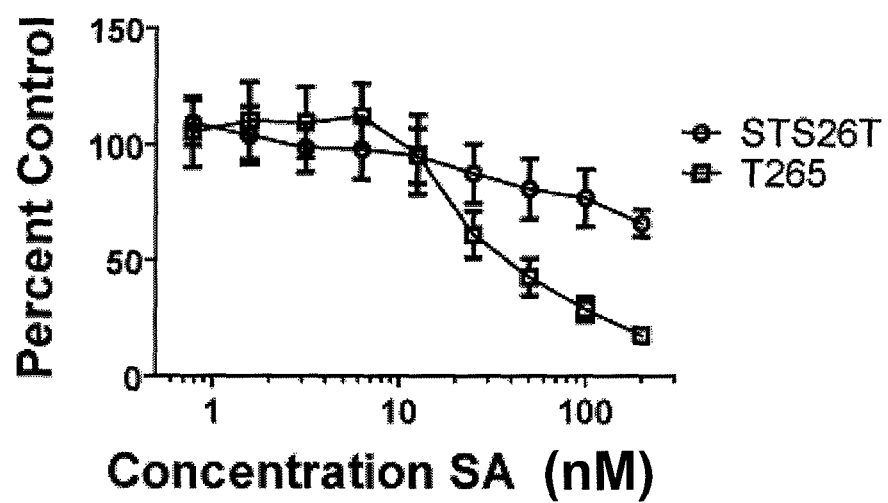
FIG. 12 is a line graph showing the human MPNST cell line T265 from an NF1 patient and sporadic human MPNST STS26T cells at varying concentrations of SA as measured by XTT assay. In accordance with an embodiment of the invention, this figure shows that T265 cells are sensitive to SA, whereas STS26T cells are not.
Figure 13A:
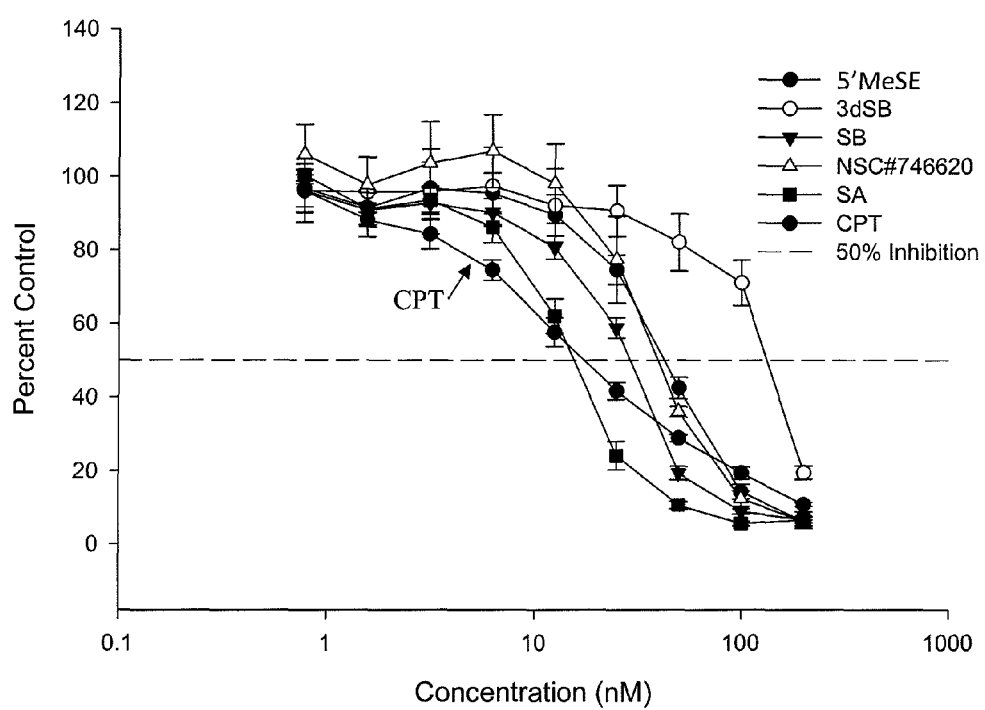
FIG. 13A is a line graph showing percent viability versus control of murine MPNST cells (K14553) at increasing concentrations of various schweinfurthins (abbreviations as for FIG. 11 and CPT is camptothecin). In accordance with an embodiment of the invention, this figure shows K14553 cells are sensitive to SA analogs.
Figure 13B:
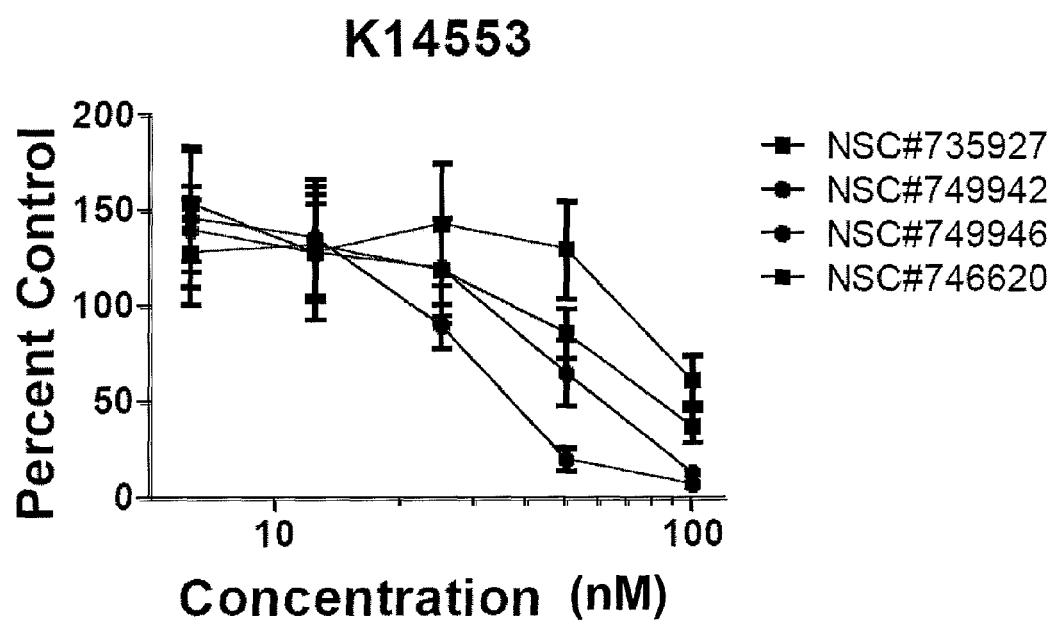
FIG. 13B is another line graph showing percent viability versus control of K14553 cells at increasing concentrations of various schweinfurthins (abbreviations as for FIG. 11 and NSC#735927 is 3-deoxyschweinfurthin B (3dSB)). In accordance with an embodiment of the invention, this figure shows K14553 cells are sensitive to SA analogs.
Figure 14:
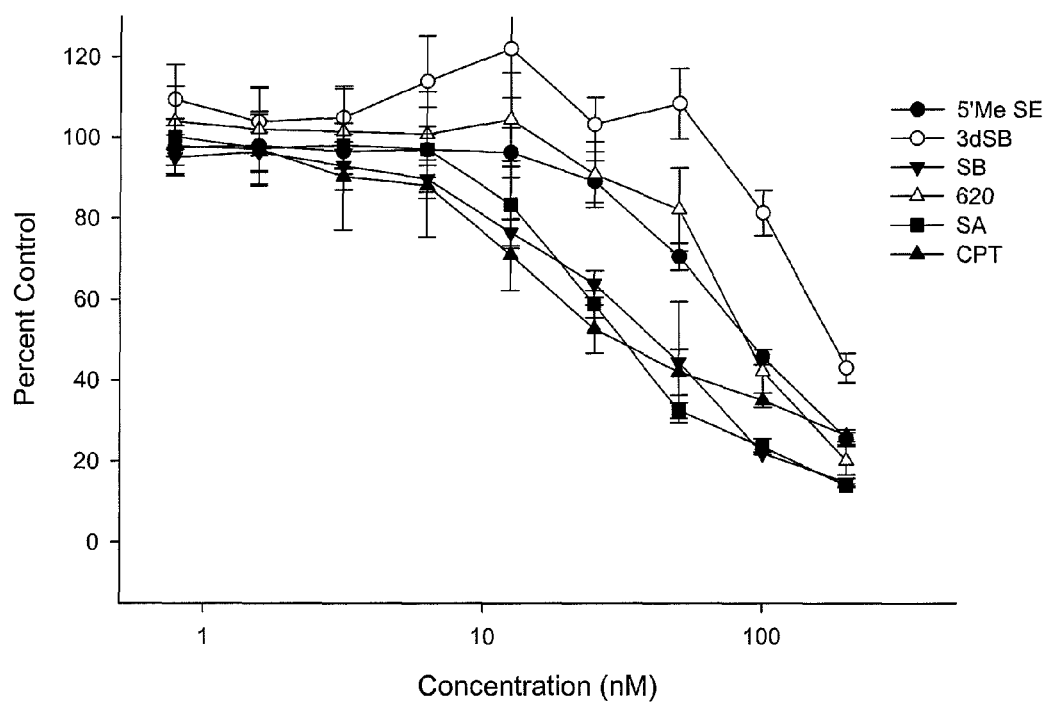
FIG. 14 is a line graph showing percent viability versus control of murine MPNST cells (K16561) at increasing concentrations of various schweinfurthins (abbreviations as above and 620 is 5′MeSG). In accordance with an embodiment of the invention, this figure shows K16561 cells are sensitive to SA analogs.

NF1 deficient tumor cells are differentially sensitive to the antiproliferative effects of SA and analogs. Given the NF1-GRD dependence of SA sensitivity in astrocytoma cells, two MPNST cell lines derived from the NPcis mouse were tested. A dose dependent inhibition of proliferation of these cells was seen (FIG. 10). Consistent with the effects of SA on Nf1-deficient astrocytoma cells, an effect on the actin cytoskeleton in the MPNST cell lines was also seen, including loss of stress fibers and reduced MLC phosphorylation. When SA was tested against the human MPNST cell line T265, derived from a NF1 patient, potent inhibition of cell proliferation was also seen (FIG. 11). In contrast, when the effect of SA on a sporadic MPNST cell line was measured, STS-26T, which has been shown to express wt NF1, much weaker inhibition of proliferation was observed (FIG. 12). Four synthetic analogs of schweinfurthin A also selectively inhibited the growth of Nf1-deficient cells (FIGS. 13A, 13B, and 14). (Camptothecin was used as a positive control since it is known that cancer cells, including A549 cells, are generally sensitive to it.) Because these tumors are not protected by the blood-brain barrier, they may be a schweinfurthin disease target regardless of whether schweinfurthins can cross the blood-brain barrier. These findings further support the model that SA targets a signaling network that is essential for tumor cell survival in NF1 deficient cells.

Figure 15:
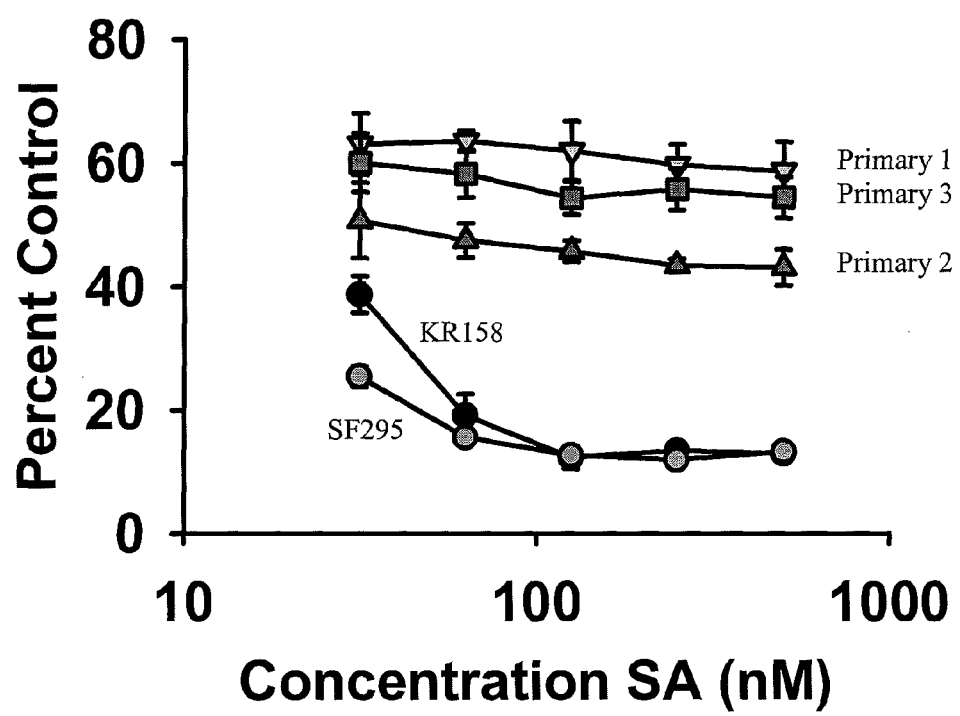
FIG. 15 is a line graph showing the percent viability versus control of KR158, SF295, and primary astrocyte cells at increasing concentrations of SA. In accordance with an embodiment of the invention, this figure shows KR158 and SF295 cells are sensitive to SA, whereas the primary astrocyte cells are not.

The specificity of schweinfurthin appears to depend on loss of neurofibromin activity, as primary astrocytes, either wild-type or Nf1−/+; Trp53−/+, are resistant to inhibition by schweinfurthin (FIG. 15). This finding suggests that there are intrinsic mechanisms within the tumor cells that make them sensitive to the compound, or that the untransformed cells are more effective at metabolizing the compound.

Nf1−/+ cells often show a haploinsufficient phenotype, and could have increased susceptibility to therapy, relative to normal cells. This data suggests that only cells that have lost or mutated the wild-type copy of Nf1 will be sensitive to schweinfurthins.

NF1 patients carry a germline mutation in the NF1 gene, such that all cells in the body have decreased NF1. There is much published data on the hypersensitivity of NF1 heterozygous cells that raises the concern that the "normal" cells of NF1 patients may respond adversely to chemotherapies against the tumors. Because schweinfurthin A shows specificity for NF1 null cells, this compound may show specific, safer efficacy for the treatment of NF 1 patients.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preventing or treating an undesirable condition in a subject carrying cells homozygous null for the neurofibromatosis type 1 gene or a subject that is haploinsufficient for the neurofibromatosis type 1 gene, comprising administering to the subject a compound or a pharmaceutical composition comprising such a compound and a pharmaceutically acceptable carrier, wherein the compound is a schweinfurthin or schweinfurthin analog or derivative, or a pharmaceutically acceptable salt, prodrug, hydrate, or solvate thereof, with the proviso that the schweinfurthin or schweinfurthin analog or derivative is not schweinfurthin A.

2. The method of claim 1, wherein the schweinfurthin is schweinfurthin B, 3-deoxyschweinfurthin B, 5'-methylschweinfurthin E, or 5'-methylschweinfurthin G.

3. The method of claim 1, wherein the schweinfurthin is schweinfurthin B, 5'-methylschweinfurthin E, or 5'-methylschweinfurthin G.

4. The method of claim 1, further comprising administering separately, simultaneously, or sequentially at least one additional compound that modulates a neurofibromatosis type 1 pathway.

5. The method of claim 4, wherein the schweinfurthin or schweinfurthin analog or derivative, pharmaceutically acceptable salt, prodrug, hydrate, or solvate and the at least one additional compound that modulates a neurofibromatosis type 1 pathway are administered simultaneously.

6. The method of claim 4, wherein the schweinfurthin or schweinfurthin analog or derivative, pharmaceutically acceptable salt, prodrug, hydrate, or solvate and the at least one additional compound that modulates a neurofibromatosis type 1 pathway are administered sequentially.

7. The method of claim 1, wherein the subject is a human.

8. The method of claim 1, wherein the undesirable condition is a tumor.

9. The method of claim 1, wherein the undesirable condition is a peripheral nervous system condition.

10. The method of claim 9, wherein the undesirable condition is a malignant peripheral nerve sheath tumor (MPNST).

11. A compound of the formula I

Formula I wherein $R^1$ is H or hydroxyl, $R^{2a}$ is H or alkyl, $R^{2b}$ is H or alkyl, and $R^3$ is H, alkyl, or alkenyl, or a pharmaceutically acceptable salt, prodrug, hydrate, or solvate thereof, with (i) the proviso that when $R^{2a}$ and $R^{2b}$ are both H or $R^{2a}$ is alkyl and $R^{2b}$ is H, then $R^3$ is not H or a $C_5$ alkenyl and (ii) the proviso that when $R^1$ is H and $R^{2a}$ and $R^{2b}$ are both alkyl, then $R^3$ is not H.

12. A compound of the formula or a pharmaceutically acceptable salt, prodrug, hydrate, or solvate thereof.

13. A pharmaceutical composition comprising (a) a compound of claim 12 or a pharmaceutically acceptable salt, prodrug, hydrate, or solvate thereof, and (b) a pharmaceutically acceptable carrier.

14. The pharmaceutical composition of claim 13, wherein the composition further comprises at least one additional compound that inhibits a ras pathway.

15. A compound of the formula

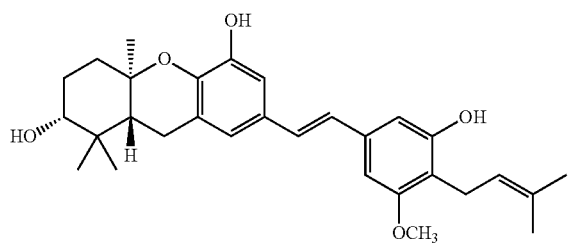 [SMILES: COc1cc(/C=C/c2cc(O)c3c(c2)C[C@@H]2C(C)(C)[C@H](O)CC[C@@]2(C)O3)cc(O)c1CC=C(C)C]

or a pharmaceutically acceptable salt, prodrug, hydrate, or solvate thereof.

16. A pharmaceutical composition comprising (a) a compound of claim 15 or a pharmaceutically acceptable salt, prodrug, hydrate, or solvate thereof, and (b) a pharmaceutically acceptable carrier.

17. The pharmaceutical composition of claim 16, wherein the composition further comprises at least one additional compound that inhibits a ras pathway.

18. A method of preventing or treating an undesirable condition in a subject carrying cells homozygous null for the neurofibromatosis type 1 gene or a subject that is haploinsufficient for the neurofibromatosis type 1 gene, comprising administering to the subject a compound or a pharmaceutical composition comprising such a compound and a pharmaceutically acceptable carrier, wherein the compound is a schweinfurthin or schweinfurthin analog or derivative, or a pharmaceutically acceptable salt, prodrug, hydrate, or solvate thereof, wherein the undesirable condition is a non-tumor manifestation of neurofibromatosis type 1.

19. The method of claim 18, wherein the schweinfurthin is schweinfurthin A, schweinfurthin B, 3-deoxyschweinfurthin B, 5'-methylschweinfurthin E, or 5'-methylschweinfurthin G.

20. The method of claim 18, wherein the non-tumor manifestation is pseudarthrosis, vasculopathy, or a learning disability.

21. A pharmaceutical composition comprising (a) a compound of claim 11 or a pharmaceutically acceptable salt, prodrug, hydrate, or solvate thereof, and (b) a pharmaceutically acceptable carrier.

22. The method of claim 1, wherein the undesirable condition is neurofibromatosis type 1.

* * * * *